United States Patent [19]
Jat et al.

[11] Patent Number: 5,688,692
[45] Date of Patent: Nov. 18, 1997

[54] TRANSGENIC MOUSE CELLS EXPRESSING TS SV40 LARGE T

[75] Inventors: Parmjit Singh Jat; Dimitris Kioussis, both of London; Mark David Noble, Berkhamstead, all of England

[73] Assignee: Ludwig Institute for Cancer Research, New York, N.Y.

[21] Appl. No.: 17,320

[22] Filed: Feb. 11, 1993

Related U.S. Application Data

[63] Continuation of Ser. No. 657,809, Feb. 20, 1991, abandoned.

[30] Foreign Application Priority Data

Feb. 20, 1990 [GB] United Kingdom ............... 9003791

[51] Int. Cl.$^6$ .................. C12N 5/00; C12N 15/00; C12P 21/06
[52] U.S. Cl. .................. 435/354; 435/325; 435/377; 435/69.1; 800/2
[58] Field of Search .................. 800/2; 435/240.1

[56] References Cited

U.S. PATENT DOCUMENTS

| | | | |
|---|---|---|---|
| 4,736,866 | 4/1988 | Leder et al. | 800/1 |
| 4,870,009 | 9/1989 | Evans et al. | 435/70 |
| 5,073,490 | 12/1991 | Babinet et al. | 435/240 |
| 5,087,571 | 2/1992 | Leder et al. | 435/240 |
| 5,270,191 | 12/1993 | McKay et al. | |

FOREIGN PATENT DOCUMENTS

| | | |
|---|---|---|
| 0289121 | 11/1988 | European Pat. Off. |
| 0351921 | 1/1990 | European Pat. Off. |
| WO8707298 | 12/1987 | WIPO |
| WO8905864 | 6/1989 | WIPO |
| WO 9004036 | 4/1990 | WIPO |
| WO9003432 | 4/1990 | WIPO |

OTHER PUBLICATIONS

Paul et al (1988) Expt. Cell Res. 175, 354–362.
Jat et al (1989) Molec. Cell Biol. 9, 1672–1681.
Kimura et al (1986) Cell 44, 261–272.
Jat et. al (1986) J. Virol. 59, 746–750.
Reyes et al (1982) Nature 297, 598–601.
Palmiter et al., Nature 457–460 (1985).
Steward et all, Cell 38: 627–637 (1984).
Brinster et al., Cell 37: 367–379 (1984).
Brinster et al., Nature 306: 332–336 (1983).
Palmiter et al., Science 222: 809–814 (1983).
Lacy et al., Cell 34: 343–358 (1983).
McKnight et al., Cell 34: 334–341 (1983).
Palmiter et al., Cell 29: 701–710 (1982).
Palmiter et al., Nature 300: 611–615 (1982).
Van Brunt, "Transgenic Primed For Research" Bio/Tech. 8: 725–757 (Aug. 1990).
Morello et al., :"Lymphorproliferative Syndrome Associated With c-myc Expression Driven by a class I Gene Promoter in Transgenic Mice", Onc. Res. 4: 111–125 (1989).
Morello et al., Oncogene 4: 955–961 (1989).
Efrat et al., Proc. Natl. Acad. Sci. USA 85: 9037–9041 (1988).
Biebereich et al., Mol. & Cell Biol. 7(11) 4003–4009 (1987).
Efrat et al., Mol. & Cell Biol. 7(1): 192–198 (1987).
Messing et al., Nature 316: 461–463 (1985).
Ritchie et al., Nature 312: 517–520(1984).
Grones et al (1993) Develop. Biol. 159, 87–104.
Kershaw et al (1994) Develop. Neurosci. 5, 2197–2200.
Morgan et al (1994) Develop. Biol. 162, 486–498.
Chambers et al (1993) Proced. Natl. Acad. Sci: 90, 5578–5582.
Noble et al (1995) Transgenic Res , in press.
Noble et al (1993) Neuroprotocols: Comp to Meth. Neurosci. 3, 189–199.
Palmiter et al (1985) Nature 316, 457–460.
Itram et al (1994) Proced. Natl., Acad Sci 91, 6448–6452.
Noble et al (1992) Brain Path. 2, 39–46.

*Primary Examiner*—Deborah Crouch
*Attorney, Agent, or Firm*—Felfe & Lynch

[57] ABSTRACT

The provision of cell lines from virtually any cell type of the animal body is greatly facilitated by transgenic non-human eukaryotic animals of the invention in which at least some cells have (i) a differentiation inhibiting sequence chromosomally incorporated under the control of a non-constitutive promotor and/or (ii) a differentiation inhibiting sequence which is itself conditionally active. Said genes are chromosomally incorporated under the control of a promotor such that expression of said sequence is normally held below an effective level, thus allowing normal cell development. However, cells taken from said animal may be prevented from completing differentiation to a non-dividing state in tissue culture by activating expression of said sequence.

18 Claims, 3 Drawing Sheets

TRANSGENIC MOUSE CELLS EXPRESSING TS SV40 LARGE T

This application is a continuation of application Ser. No. 07/657,809 filed Feb. 20, 1991, now abandoned.

This invention relates to "conditionally" transgenic non-human vertebrate animals, e.g. mammals, in which germ and/or somatic cells have chromosomally incorporated therein a nucleic acid sequence or sequences expression of which, during normal animal development, is inhibited but which may be activated in isolated tissue culture. The invention is also concerned with such isolated cultures and their use in producing immortalized cell lines. Such cell lines in turn have many useful applications.

The study of physiological function on the cellular level has greatly benefited from the availability of cell lines which allow biochemical experimentation to be conducted on homogeneous populations of clonally derived cells. Such cell lines have frequently been derived from tumours of either spontaneous or experimental origin. More recently, it has become possible to use genetic manipulations to create cell lines by the insertion of particular types of genetic information into the cellular genome.

The various types of genetic information which allow the generation of cell lines share the property of preventing cells from differentiating into a non-dividing end-stage cell. In Virology 127, 74–82 (1983), Petit et al described the use of SV40 in the immortalization of rodent embryo fibroblasts, and numerous studies have defined differentiation inhibiting genes by their ability to rescue fibroblasts from entry into a phenotype of senescence, a phenotype normally seen after a limited number of fibroblast divisions. In terms of generation of cell lines, the entry of fibroblasts into such a senescent phenotype is sometimes called "crisis", and the ability to rescue cells from entry into crisis provides a valuable assay system for the identification of genes in this family. As the cells in which this particular type of genetic information is expressed can be established as tissue culture lines which will grow for effectively infinite periods in vitro, this family of genes has been called the establishment genes or immortalizing genes (Land et al, Nature 1983, 304, 596–602, Ruley Nature 1983, 304, 602–606). As these genes also inhibit end-stage differentiation, they are also sometimes called maturation arrest genes.

Current analysis suggests that the differentiation inhibiting genes are frequently members of a family of oncogenes called the nuclear oncogenes. These nuclear oncogenes include a number of viral oncogenes which as yet have no known cellular counterparts (e.g. SV40 large T antigen, polyoma large T antigen, human papilloma virus E7 antigen) (Jat & Sharp 1986, J. Virology 59, 746–750, Rassoulzadegan et al, 1982 Nature 300, 713–718, 1983 PNAS 80, 4354–4358, Phelps et al, 1988 Cell 53, 539–547, and Petit et al supra) and also a number of genes with known cellular homologues (of which myc is the best example). In addition, some genes in the family of cytoplasmic (or growth-controlling) oncogenes also inhibit differentiation in some cell types. For example, the src gene inhibits differentiation of glial progenitor cells. It is however rare for genes thought to function in the stimulation of cell division also to have the capacity to inhibit cellular differentiation processes.

In recent experiments a variety of methods have been used to place immortalizing oncogenes into cells to allow the establishment of cell lines. For example, in Molecular and Cellular Biology Vol 6, p.1204–1217 (April 1986), Jat et al described a murine retrovirus shuttle vector system and its use to construct recombinant retroviruses for infection of rat F111 cells. Resultant cell lines which expressed SV40 large T were not tumorigenic but exhibited efficient microcolony formation (in soft agar). Moreover, using these recombinant retroviruses, they showed that the SV40 large T antigen by itself is capable of efficiently immortalizing primary fibroblasts without crisis (Jat and Sharp supra).

Various types of transfection strategies exist, and retroviral-mediated gene insertion is the most commonly used strategy for introducing immortalizing genetic elements. These strategies share a number of disadvantages. First, there is at present no means of targeting specific cellular populations. Second, the efficiency of effective gene insertion is low (of the order of 1 in $10^4$ cells or less) and therefore requires the use of large numbers of cells in order to establish cell lines with any regularity. Third, effective integration of the genetic element requires the induction of cell division in tissue culture. Fourth, extended growth in tissue culture is required before cells can be used in experimentation, and this growth usually involves a period of time in artificial conditions which impose highly artificial selective pressure on cell populations.

It would be of great value to have a method which would allow cell lines to be established from a wide variety of cell types with an efficiency and reliability greater than that available with present technology.

In addition, all cells of the body can be divided into the two different classes of precursor cells and end-stage cells. Precursor cells (which include progenitor cells and stem cells) are the cells involved in replenishment of specific cellular populations within the body. They can be restricted to the production of only one type of end-stage cell (e.g., skeletal muscle precursors are thought to give rise to only skeletal muscle), they can be bipotential (e.g., granulocyte-macrophage progenitor cells give rise only to granulocytes and macrophages), or they can give rise to a multiplicity of cell-types (e.g., haematopoetic stem cells give rise to all the cells of the bloodstream, and embryonic stem cells can give rise to all of the cell-types of the body). In contrast, end-stage cells represent cells which have reached a final point in their differentiation pathway, and are no longer capable of generating a multiplicity of cell types or, more importantly, of taking part in replenishment of damaged tissue populations.

There are a small number of instances, all of them involving the haematopoetic system, where sufficient knowledge about specific precursor cells exists to permit restoration of normal tissue function by using a primitive form of precursor transplantation therapy to replace both precursor cells and differentiated end-stage cells. This primitive form of precursor therapy is the principle behind the widely-used bone marrow transplant, which works by the emplacement of haematopoetic stem cells (along with other cells) from a donor individual into a recipient suffering from depletion of some or all of their normal haematopoetic populations (frequently as a result of radiotherapy to treat a disseminated malignancy). The infected haematopoetic stem cells colonize the patient's own bone marrow, and go on to produce magakaryocytes, lymphocytes, macrophages, eosinophils and all of the other diverse cell types derived from this single stem cell population.

Although there are many areas of contemporary and future scientific and medical practice where the ability to carry out precursor replacement therapy could be of significant value, efforts in this direction are presently frustrated by the paucity of current knowledge about the identity of the precursor populations which contribute to the normal development of most tissues of the body. Despite the many years of work which has gone into the study of these populations, there are only a limited number of instances where specific precursor populations have been identified and can be manipulated in tissue culture in a manner which might allow them to be subsequently introduced into damaged tissue. Similarly, there are only a limited number of instances in which the identity of the molecular signals which cause precursors to divide or to differentiate along specific pathways is know. Obtaining such knowledge, which could be of great value in causing the body's own precursor populations to more effectively replenish themselves or repair damaged tissue, is hampered enormously by the lack of suitable cellular assay systems and also by the lack of suitable source materials for the purification of these important molecules.

In WO89/09816, McKay et al described a general method of immortalizing cell lines in which a growth promoting gene is introduced into vertebrate cells. The intention is that function of this gene be controlled by an external factor or factors so that the gene function can be regulated at will. It is stated that precursor cells may then be grown with the gene activated, and the resulting cell population then allowed to differentiate by inactivating the gene by changing the conditions to "non-permissive" conditions. In addition, Almazan et al, at the 18th Annual Meeting of the Society for Neuroscience, Toronto, (November 1988) (see Soc. Neurosci. Abstr. 14(2) 1988 1130), described the immortalization of an oligodendrocyte precursor cell using a temperature sensitive oncogene-carrying retrovirus.

However, although the utilization of existing techniques to insert genes into precursor cells has allowed for the development of particular cell lines with precursor qualities, not only do the problems inherent in the generation of any cell lines apply also to the generation of precursor cell lines, but the establishment of precursor cell lines suffers from the further difficulty that precursors may represent only a small fraction of the cells in any given tissue, and the possibility of successfully introducing the required genetic information into the cells is correspondingly reduced.

So-called "transgenic" animals have also been known for some years, i.e. animals having incorporated into the animal genome a foreign gene or genes which may be expressed in their new chromosomal environment to change the characteristics of the animal in a directed manner.

Papers on transgenic animals first appeared in the literature in 1982. Thus, Palmiter et al. (Cell, 1982, 29:701–710) microinjected a plasmid containing the mouse metallothionein-I promotor/regulatory region joined to the structural gene of herpes virus thymidine kinase. They showed expression of the hybrid gene in vivo and regulatability of the gene in vivo by heavy metals. Gordon and Ruddle (Prog. Clin. Biol. Res., 1982, 85:111–124) also demonstrated inheritance of injected DNA sequences. Palmiter et al (Nature, 1982: 611–615) showed that mice transgenic for growth hormone, as regulated by the metallothionien promotor, grew to abnormally large size.

In 1983, McKnight et al. (Cell 1983, 32:335–341), Lacy et al (Cell, 1983, 34:343–358), Palmiter, et al. (Science, 1983, 22:809–814), Brinster et al (Nature, 306:332–336), and Gordon (J. Exp. Zool., 1983, 228:313–324) all reported on characterization of transgenic animals without discussion of cell growth in tissue culture.

In 1984 the first papers indicating that the expression of oncogenes would disrupt normal development appeared. Brinster et al. (Cell, 1984, 37:367–379) demonstrated that mice expressing SV40 large T antigen under the control of the metallothionien promotor developed tumours of the choroid plexus. Tumours developed long after birth, indicating the involvement of more than just the transgene in tumour formation. Cell lines were derived from tumour tissue, but no discussion is offered on attempts to drive cell lines from pre-tumourous tissue or from other tissues. Slightly later, Stewart et al. (Cell, 1984, 38:627–637) reported that mice expressing c-myc under the control of a hormonally inducible mouse mammary tumour virus promotor developed mammary adenocarcinomas. There is no discussion of cell lines. The ability to use cells from transgenic mice in culture was also discussed by Ritchies et al. (Nature, 1984, 312:517–520), who showed that it was possible to make hybridomas by fusing spleen cells from mice transgenic for the immunoglobulin kappa gene with normal hybridoma fusion partners.

In U.S. Pat. No. 4,736,866, Leder and Stewart describe transgenic non-human mammals in which the germ and somatic cells contain an activated oncogene sequence. Such animals are, inter alia, useful models for the testing of anti-cancer drugs due to their increased tendency to develop neoplasms, and the lower level of drug dosage that can consequently be employed in such testing. The animals do, however, exhibit a pronounced tendency to develop abnormally, and this virtually eliminates their usefulness as models for normal cell development studies or as sources of therapeutic biological materials.

Palmiter et al. (Nature, 1985, 316:457–460), continuing a previous analysis of the effects of SV40 large T antigen in transgenic mice, showed that the development of choroid plexus tumours required the presence of the SV40 enhancer region, and that different SV40 constructs yielded different types of tumours. Cell lines were isolated from hepatocellular tumours of some mice, and these cells were shown to express T antigen in their nuclei. The authors described production of mice with the ts58 temperature-sensitive derivative of SV40, but stated that this construct was not temperature-sensitive. Despite the widespread use of T antigen in the creation of transgenic mice and the widespread use of the ts58 (=tsA58) mutant in the generation of conditionally immoral cell lines in vitro through the use of, e.g., retroviral-mediated gene insertion, no other work in the prior art (including later work of Palmiter and colleagues) returned to the use of this mutant.

It can be said that the general goal in transgenic work reported thus far has been to introduce into the germline genetic information which disrupts normal development, generally of specific tissues. In complete contrast, as will be clear hereinafter, the present invention is concerned with the creation of transgenic animals in which normal development is not disrupted, but from which cells can be harvested, inter alia, in which activation of the transgenes in tissue culture will specifically facilitate the study of cells from potentially all tissues of the body.

Thus, for example, even though other laboratories have previously gone so far as to build genetic constructs in which a regulatable promoter (H-2K$^b$) has been used to regular oncogene expression, the possibility that use of such promotors in transgenic animals might allow conditional oncogene expression in vitro has not previously been recognized. The most detailed example of this is the studies linking the H-2K$^b$ promotor with the c-myc gene described by Morello et al. (Oncogene Research, 1989, 4:111–125), who constructed several transgenic strains carrying a fusion gene in which the 5' H-2K$^b$ promotor sequences were linked to the human c-myc proto-oncogene in order to determine whether constitutive c-myc expression was found in all tissues and to ascertain the biological effects in such constitutively enforced myc expression in these transgenic animals. The authors obtained 33 mice which led to the establishment of 5 transgenic strains. The authors reported expression of the H-2/myc construct in most organs analyzed, with maximal expression in the lymphoid organs and minimal expression in the brain and in the liver. The level of expression of H-2K/myc was in parallel with the expression of H-2K. Morello et al. also reported that no pathology was observed over a period of 20 months in four of the H-2K/myc mice, and concluded from this that a second genetic event was necessary for immortalization with this construct.

In earlier transgenic work, Efrat and Hanahan (Mol. Cell Biol., 1987, 7:192–198) examined cell-specific activity of a reverse promotor element in two lineages of transgenic mice in which the promotor was used to target T antigen expression to the beta islet cells of the pancreas. Expression of the gene was examined in tumour cells. Also, Efrat et al. (Proc. Natl. Acad. Sci. USA, 1988, 85:9037–9041) examined the behaviour of three pancreatic beta-cell lines established from insulinomas derived from transgenic mice carrying a hybrid insulin-promotor SV40 T antigen gene. The beta tumour cells, which were all derived from primary beta-cell tumours, maintained the features of beta cells for 50 passages in culture. The authors concluded that "targeted expression of an oncogene with a cell-specific regulatory element can be used both to immortalize a rare cell type and to provide a selection for the maintenance of its differentiated phenotype". In the present invention, an important contribution to the science is that "targeted expression" is not necessary. As will be clear hereinafter, the present transgenic animals can be storehouses of cell types which can be chosen and taken at will, when desired, for immortalization.

In yet other transgenic work, Bieberich et al. (Mol. Cell Biol., 1987, 7:4003–4009) also used transgenic mice to study class I antigen function, and found that skin grafts from transgenic mice were rapidly rejected by mice of the background strain, that the class 1 transgene was inducible by interferon treatment and suppressible by human adenovirus 12 transformation.

Also in 1987, Choi et al. (J. Virol., 1987, 61:3013–3019) examined expression of simian virus 40 early region genes under transcriptional control of the mouse mammary tumor virus long terminal repeat. Cells cultured from the transgenic animals showed expression of the chimeric gene which was inducible by glucocorticoids. Many, but not all, tissues which expressed the simian virus 40 sequences showed premalignant features and developed into tumours.

In 1988, Paul et al. (Klin Wochenstr., 1988, 66, Suppl. 11:134–139; Exp. Cell Res., 175, 354–365) created permanently growing hepatocyte lines by growing liver cells from mice expressing SV40 virus sequences driven by the mouse metallothionein enhancer sequence. Most hepatocytes in the liver displayed an immortalized phenotype in culture, and became increasingly transformed-like with further growth in culture. Although the initial cells were nonmalignant, they clearly differed from normal cells in that cells did not require addition of epidermal growth factor to chemically defined medium to promote cell division. In vivo, the mice developed hepatocellular carcinomas.

MacKay et al. (Kidney Int., 1988, 33:677–684) established permanent cell lines of cloned glomerular epithelial, mesangial and endothelial cells from a line of mice transgenic for simmian virus 40. These mice appeared normal at birth but by 3 to 4 months of age had sclerosis affecting a variable percentage of their glomeruli. The cells derived from these mice maintained features characteristic of their normal counterparts despite their transformed phenotype.

Langdon et al. (Oncogene Res., 1988, 3:271–279) studied the growth of E mu-myc transgenic B-lymphoid cells in vitro to examine their progression to lymphomatous characteristics. Results demonstrated that cells initially required bone marrow feeder layers, after which cultures resolved to monoclonal or oligoclonal composition and then only at a later point achieved growth autonomy, thus indicating the importance of multiple events in establishing growth autonomy.

In WO89/09816, supra, there is a suggestion that it may be possible to introduce the conditionally immortalized cells described therein into animals, and thereby produce transgenic animals in which the growth promoting gene present in said cells is inactive at normal body temperatures. However, the work described does not take up this suggestion, and how such a technique should be successfully applied is simply not described. There is no disclosure of a promotion system or conditional oncogene producing only low levels of expression as are used in the present invention (see below), nor is there any disclosure of the use of a stable transgenic animal as a source of cells, differentiated or precursor cells (which later may be immortalized in culture).

It would clearly be highly desirable to provide a method for efficiently obtaining cell lines from potentially any tissue of the body. That is a goal which, aside from specific problems noted above, and even with the immense interest in transgenic animals, has not hitherto come remotely close to realization in the art.

The present invention provides in one aspect a transgenic non-human eukaryotic animal having germ cells and/or somatic cells into which a differentiation inhibiting sequence has been chromosomally incorporated under the control of a non-constitutive promotor such that expression of said sequence is normally inhibited allowing normal cell development, but precursor cells taken from said animal may be prevented from completing differentiation in tissue culture by providing permissive conditions for said promotor thereby activating expression of said sequence. In connection with these "conditional" transgenic animals, by "non-constitutive promotor" as used herein is meant a promotor system which: (a) can be induced to cause much higher levels of expression of the sequence under its control than occur in the absence of induction, and (b) in the absence of induction either does not detectably permit expression or permits expression only at a level which does not inhibit normal cell development. It will be appreciated that a promotor system which is "leaky" or which does permit a small amount of expression may be tolerated if the level of expression fails to impede a normal development pattern. As will be apparent, there are various ways in which expression levels may be kept down in the animals but still be induced to rise when desired. "Conditionality" may thus be achieved using multiple means, as in the specific work described herein which uses a form of double conditionality involving a conditional oncogene. Multiple conditionality may, for example, alternatively depend upon the use of a promotor system employing two or more regulatory genetic elements, the regulation of all of which is necessary to cause the higher levels of expression referred to in (a) above to be achieved.

In another aspect, the invention relates to a transgenic non-human animal having cells into which a differentiation inhibiting sequence had been chromosomally incorporated under the control of a non-constitutive promotor, wherein expression of said differentiation inhibiting sequence is inhibited in the absence of activation for said non constitutive promotor.

Well differentiated cell types can, if desired, be effectively put into tissue culture from such animals, and, in addition, the present invention provides a method for obtaining precursor cells from normal tissue in a manner which greatly improves the potential for understanding not only the identity of these cells but also the biological principles which regulate their development.

The present invention, by its achievement of low expression levels in vivo in the absence of induction, enables successful creation of transgenic animals in which development and differentiation of tissues occurs normally in vivo, providing a storehouse of biological material for various purposes.

In general, the invention concerns transgenic non-human eukaryotic animals with germ cells and/or somatic cells which contain a differentiation inhibiting DNA sequence which is inactive in most, or all, tissues of the normal animal and which is constructed so as to specifically have the minimum possible effects on normal development of the animal. Activation of the genetic construct, which is capable of preventing terminal differentiation, is preferentially achieved through manipulation of dissected tissue in vitro, although the constructs can also be activated in vivo.

Thus, in another aspect, the invention provides a transgenic non-human eukaryotic animal having germ cells and/ or somatic cells into which a differentiation inhibiting sequence which is itself conditionally active and inducible has been chromosomally incorporated under the control of a promotor such that expression of said sequence is normally held below an effective level thus allowing normal cell development but precursor cells taken from said animal may be prevented from completing differentiation in tissue culture by activating expression of said sequence.

In animals of the type defined immediately above, the conditionally active differentiation inhibiting sequence may be TAgts and/or the promotor may be a "weak" non-inducible promotor, e.g. the TK promotor. It will be appreciated by the skilled reader that molecular engineering of any of a large number of promotors (as reviewed in, for example, Levine and Manley, Cell, 1989, 59:405–408, Abel and Maniatis, Nature, 1989, 341:24–25, and Mitchell and Tjian, Science, 1989, 245:371–378 will enable the creation of weak, non-inducible promotors also suitable for use in the present invention.

In a further aspect, the invention includes a cell which has been isolated from an animal as defined above or which has been derived from such an isolated cell and which has chromosomally incorporated therein said differentiation inhibiting sequence expression of which may be activated.

The invention also includes a cell line derived from such a cell and which has been immortalized by activating expression of said differentiation inhibiting sequence.

In yet a further aspect, the invention includes a differentiated cell derived either from a cell as defined above by allowing it to differentiate without activation of expression of said differentiation inhibiting sequence or from a cell line as defined by deactivating expression of said differentiation inhibiting sequence or from a cell as defined above wherein expression of said differentiation inhibiting sequence has been activated but which cell may nonetheless be induced to differentiate by exposure to an external factor and has been so exposed.

The invention also includes a method of producing a transgenic non-human eukaryotic animal having cells into which a differentiation inhibiting sequence has been chromosomally incorporated but in a regulatable manner such that expression of said sequence may be activated but is normally inhibited allowing normal cell development, comprising effecting chromosomal incorporation of said differentiation inhibiting sequence under the control of a non-constitutive promotor into at least some cells of said animal or effecting chromosomal incorporation of a differentiation inhibiting sequence which is itself conditionally active and inducible into at least some cells of said animal.

The technique used to achieve transgenesis is immaterial to the inventive concept, but normally micro-injection at the embryonic stage is the preferred route using procedures well known in the art. Micro-injection can be used at any developmental stage from the unicellular stage to later embryonic stages.

Transgenic animals can, however, be generated in a variety of ways, all of which are to be seen as encompassed within this invention. The genetic construct can be inserted into embryonic stem cells, and these genetically manipulated stem cells can be injected into fertilized zygotes at a stage where a small number of cells are present. The embryonic stem cells in some cases become incorporated successfully in the zygote and cells derived from these genetically manipulated cells can differentiate to form many or all of the cell types found in the body. In some animals, such cells will also contribute to the germ line, thus providing a means of making fully transgenic animals as progeny from the initial chimaeras. It has also been suggested that sperm themselves can be used as a vector for creating transgenic animals (although this claim is currently considered controversial) and so the possibility of incorporation as a result of events at a preconception stage should not be discounted. The manner and timing (in animal developmental terms) of achieving chromosomal incorporation in accordance with the invention does not matter, provided that the differentiation inhibiting sequence ultimately appears in at least some cells of a transgenic animal under the control of a non-constitutive promotor so that the sequence is regulatable.

The central feature of this invention is the intent to avoid a level of expression of the experimentally-introduced genetic information such that normal development is impeded. This feature distinguishes the present invention from all other transgenic experimentation thus far reported. This necessary aspect of the present invention is principally achieved by utilizing promotor sequences which must be specifically activated in order to allow appreciable expression of the differentiation inhibiting gene. In the non-limiting Examples provided hereinafter, oncogene function is further limited by using an oncogene sequence which itself is only conditionally active. The invention accordingly envisages the principle of multiple conditionality. This may be achieved, for example, by the use of a plurality of genetic regulatory elements which, used in concert, provide an overall non-constitutive promotor system as defined above, or it may be achieved by the use of one or more genetic regulatory elements and conditional oncogene-like sequences which, again, used in concert, achieved the desired effect thus providing such a system.

The differentiation inhibiting sequences relevant to this invention, are capable of inhibiting differentiation of precursor cells. Such sequences or genes include oncogenes which encode for proteins which localize to cellular nuclei. A number of these nuclear oncogenes have the ability to immortalize cells (and thus render them capable of growth for indefinite periods without entering a state of terminal differentiation) and also to inhibit the differentiation of precursor cells into non-dividing end-stage cells. Several of these genes are not only of viral origin but also have, at present, no known mammalian counterparts in the normal genome. For example, the normal cellular counterparts of SV40 large T antigen, human papilloma virus E7 protein and polyoma large T antigen are currently unknown, even though it has bene shown that all of these viral proteins are able to interact with normal cellular proteins in a manner thought to be related to the function of the viral proteins in neoplastic transformation (Whyte P. et al, 1988 Nature 388, 124–129, De Caprio J. A. et al. 1988 Cell 54, 275–283, and Dyson N. et al, 1989 Science 243, 934–937). Some normal cellular proteins which localize to the nucleus, such as c-myc, also are able to immortalize cells and inhibit precursor cell differentiation (Land et al supra, Dotto G. P. et al, 1985 Nature 318, 472–475, and Dmitrovsky E. et al, 1986 Nature 311, 748–750). In addition, a small number of oncogenes thought to be associated with growth regulation, such as src, have the ability to immortalize and inhibit the differentiation of specific precursor populations.

Broadly, it can be stated that at present there are five diverse groups of genes which may function as differentiation inhibiting sequences in this invention. Some of the known genes in each category are listed in the Table below. The first category of genes are members of the nuclear oncogene family, and include genes like SV40 large T antigen and also genes like myc and myb. The second category of genes are those which can be converted by mutation from suppressor genes to immortalizing genes. The one representative of this category known at present is $p^{53}$, which appears to interact in an as yet unknown manner with the family of proteins also involved in modulation of the retinoblastoma gene product activity. The third category of genes are those commonly thought to be involved in control of cell proliferation, but which also appear to be able to inhibit the differentiation of some cell types. The fourth category of genes are typified by a secreted molecule called differentiation inhibiting activity, which seems to work through cell-surface receptors to inhibit the differentiation of embryonic stem cells. Finally, it has recently been discovered that co-operative interactions between mitogens can also inhibit precursor cell differentiation. In studies on the oligodendrocyte-type 2 astrocyte progenitor cell of the rat optic nerve, it has been found that stimulation of these precursor cells simultaneously with platelet-derived growth factor and basic fibroblast growth factor completely inhibits differentiation of precursors into oligodendrocytes and allows 0–2A progenitors to be grown indefinitely in tissue culture in the apparent absence of mutational activation of nuclear oncogenes (Bogler et al., 1990, Proc. Natl. Acad. Sci. USA. 87:6368–6372). These last two sets of results indicate that it may be possible also to use soluble factors, controlled by inducible, non-constitutive promotors, to inhibit differentiation of cells. In such circumstances, the "differentiation inhibiting sequence" used in the invention is the genetic sequence encoding said factors.

TABLE

Nuclear oncogenes
  SV40 large T
  polyoma large T
  adenovirus EIA
  HPV E7 and E6
  myc
  erb A
  myb
dominant mutations altering tumour suppressor genes
  some mutants of p53
growth regulatory genes which inhibit differentiation
  V-src
genes which produce differentiation inhibiting agents
  differentiation inhibiting activity
genetic sequences encoding combinations of growth factors which work to inhibit differentiation
  platelet-derived growth factor+basic fibroblast growth factor.

Lists of nuclear oncogenes, which are most frequently the genes having differentiation inhibiting capability, have recently been compiled by Hunter (Cell, 1990, 64:249–270).

The differentiation inhibiting sequences used in the present invention are included in the genome in a manner which limits the potential of the immortalizing gene to function in vivo. For example, a thermolabile form of the SV40 large T antigen (TAg) (Tegtmeyer, 1975 J. Virology 15, 613–618) may be used which is rapidly degraded and thus inactivated at the normal body temperature of the mouse (39.5° C.). In an embodiment of this invention this temperature-sensitive TAg (TAgts) is placed under the control of a promotor which normally controls expression of Class I antigens of the major histocompatability complex (Kimura et al, 1986 Cell 44, 261–272, and Baldwin Jr. A. S. et al, 1987 Mol. Cell Biol. 7, 305–313). This promotor can be activated by exposure to gamma interferon, but is normally active only at low levels in most tissues of the body of healthy animals.

The rationale behind the use of a controllable, non-constitutive promotor is to inhibit expression of the gene of interest, expect when such expression is desired. Non-constitutive promotors which are usable in the present invention are regulatable by changing the conditions. Under certain conditions (non-permissive) the promotor function is inhibited and normal cellular development takes place. If the conditions are changed (e.g., in the example referred to above, by exposure to gamma interferon) to be permissive, appreciable expression occurs. Avoiding appreciable expression is critical, as it is known that revertant mutations of a conditional oncogene itself would be likely to cause abnormal development if the oncogene were allowed to be expressed in all tissues at all times, that low levels of activity of a conditional oncogene might become effective if high enough levels of the gene product are expressed (as described in the Example 1 hereinafter), and expression of functional levels of wild-type differentiation inhibiting sequences in vivo causes tissue transformation (as demonstrated by such other transgenic models as those offered by, e.g., U.S. Pat. No. 4,736,866).

Revertant mutations which occur by random mutation seem to occur with a frequency of 1 in $10^6$ cells. As the body of an animal contains many more than $10^{12}$ cells, this means that many cells of the body will express revertant mutations of the conditional gene. Moreover, experimentation in tissue culture indicates that revertant mutations which involve other cellular control pathways may even occur at frequencies of up to 1 in $10^4$. Thus, every tissue in the body would be expected to carry large numbers of cells which would be expressing, say, a functional oncogene capable of inhibiting normal pathways of differentiation. Such a situation is incompatible with normal development. Indeed, prior to the realization of this critical concept, unpublished attempts were made by one of the inventors (P. Jat) and colleagues to create transgenic mice in which TAgts was placed under control of the promotor for beta-actin, which would cause TAgts to be constitutively expressed at a reasonably high level in every cell of the body. Such genetic constructs do not appear to be compatible with survival of the manipulated embryo. Therefore to circumvent the problem of reversion it is essential to use a promotor which dampens expression of TAgts to below an effective level.

Another possible promotor system for use in this invention would be one based on a lactose (lac) inducible operon isolated from bacteria. The lac-inducible system is based on having binding sites for a particular protein located between the transcriptional promotor and the transcriptional start sites. Normally, the repressor binds to the operator and sterically hinders transcription. When the inducer substance is present in the cell, it complexes the repressor and prevents it binding to the operator and thereby allows transcription to occur. The specific inducer used is the allo-lactose analogue IPTG, which is non-metabolizeable and does not occur naturally. Lactose can also activate this inducer, but lactose is rapidly metabolized and is present at low levels in almost all tissues. The one bodily fluid known to contain high levels of lactose is milk, raising the possibility that this construct would be induced in the milk-producing cells of lactating females. Unlike Class I antigens, which are expressed by many cells in both a constitutive and inducible manner (resulting in an increased level of expression as compared to the situation before induction), the lac repressor may yield a still tighter control of expression of the differentiation inhibiting genes used in the present transgenic animals. The lac system is also, of course, known to operate in mammalian cells.

The lac-inducible promotor is the one known example of a bacterial promotor which can be activated by a substance which is not likely to cause induction in normal warm-blooded animals, but one can envisage that other analogous bacterial promotor systems will be discovered. In addition, it would be possible to use mutant forms of bacterials promotors, as exemplified by the lap mutation of the lac repressor. Such promotors could be used in the method of this invention.

A further example of an inducible promotor is the metallothionein promotor, which is activated by the heavy metals zinc and cadmium. This promotor could also be used in the method of this invention.

The MMTV promotor, which is regulated by glucocorticoids, is an inducible promotor which has been used in transgenic experimentation. This promotor, however, suffers from the liability that endogenous glucocorticoid production would activate expression of the differentiation inhibiting construct.

At least two advantages of the Class I promotor system can be cited, apart from its general applicability across the animal kingdom (see below). First, in those tissues in which there is a low level of endogenous Class I antigen expression, the level of activity of this promotor appears normally to be too low to support production of, say, sufficient TAgtsA58 antigen to interfere with normal development. However, addition of an inducer (e.g., gamma interferon) can superinduce activity of this promotor and bring levels of TAgtsA58 antigen to a level where full activity of the differentiation inhibiting gene can be seen. Moreover, the use of this promotor allows expression of, say, TAgtsA58 to be induced in tissues which there is normally no Class I antigen expression (such as the central nervous system) because essentially all cells have functional interferon receptors.

A major advantage of the present invention is that the general concepts developed can be applied to all species of warm-blooded animals. For example, in the example referred to above, the Class I promotor normally causes high levels of expression of major histocompatability complex genes when cells are exposed to gamma interferon (Wallach D. et al, Nature 299, Q33–836). This pathway of gene activation is already certainly known to occur in humans, bovines, rats, and mice, and seems likely therefore to occur in all warm-blooded animals. In addition, as already mentioned, the bacterial lac promotor is known to operate in mammalian cells.

The animals of this invention can be used as a source material for the growth, identification, purification and detailed analysis of, inter alia, precursor cells from potentially all tissues of the body (Morston G. et al, Hemopoietic Growth Factors, A. Review Cancer Research 1988, 48, 5624–5637). Dissected tissue can be placed into tissue culture in conditions which activate the immortalizing/ differentiation inhibiting gene, and precursor cells can then be grown indefinitely. In addition, cells not normally thought of as precursor cells (such as fibroblasts) can also be immortalized by the experimental manipulations which form a part of this invention. As previously indicated, the animals of this invention differ from the animals of U.S. Pat. No. 4,736,866 in that they are not suitable for testing of carcinogens or for testing of materials thought to confer protection against the development of neoplasms. Generally, the tissues of the animals of the present invention undergo normal development until the time they are placed in tissue culture. In the case of the present performed work, normal development has been experienced with the exception of the thymus (which shows a delayed hyperplastic enlargement of the entire organ), and even within the thymus the function of the genetic construct which prevents terminal differentiation is itself conditional. Evidence exists that cells which have been subjected to abnormal developmental conditions (as in U.S. Pat. No. 4,736,866) do not express the properties of normal cells, and that such cells are also predisposed to undergo further mutations which activate oncogenes. Thus, cells harvested from the tissues of animals which express activated oncogenes in vivo may be unreliable as suitable models for the study of normal cells, and particularly for the study of normal precursor cells. In contrast, cells isolated from the tissues of the animals described in the present invention are expected to have undergone normal development, and when grown in vitro can be expected to be as close to their normal counterparts as it is possible to be once a cell expresses an immortalizing protein.

Accordingly, another aspect of the invention provides a method of providing immortalized cells, which method comprises isolating from an animal of the invention precursor or differentiated cells having chromosomally incorporated therein said differentiation inhibiting sequence and subjecting said cells to conditions in tissue culture whereby expression of said differentiation inhibiting sequence is activated.

Preventing levels of oncogene expression which might perturb normal development could also theoretically be achieved by manipulation of the promotor system to create still finer tuning mechanisms than exist with a single genetic control element. For example, a theoretically useful promotor system would be that described by Reid et al., Proc. Natl. Acad. Sci., USA., 1989, 86:840 –844, in which the thymidine kinase promotor (which is constitutively expressed at low levels) is put downstream of a short (18 nucleotide) sequence which is sufficient for conferring inducibility with interferon onto the TK promotor. This promotor construct could theoretically be used to drive expression of tsA58 and thus lower the basal constitutive level of expression while still retaining the interferon inducibility.

It is also possible to extend the principle of dual conditionality offered herein, in which the expression of the thermolabile TAgtsA58 mutant of SV40 is controlled by the promotor elements of the Class I antigen gene. This could be extended by the use of other temperature-sensitive genes with the capacity of inhibiting normal differentiation. In addition, it is possible to build chimeric oncogenes which are rendered conditional by virtue of containing a hormone receptor sequence which is essential for oncogene function. Examples of such proteins are discussed by Picard et al. (Cell, 1988, 54:1073–1080) and Eilers et al. (Nature, 1989, 340:66–68), who have produced adenovirus E1A protein with a hormone binding domain of the rat glucocorticoid receptor and myc protein with the binding domain of the human estrogen receptor, respectively. In both instances, the effect of the chimeric protein on host cell function is dependent upon binding of the appropriate hormone to the chimeric protein.

In a particular embodiment of the present invention, the differentiation inhibiting sequence or gene used is a temperature sensitive large T antigen derived from simian virus SV40. The utilization of this gene imparts a secondary level of control on gene activity during normal development, in that the protein encoded by this mutant gene is rapidly degraded at temperatures approximating those of the normal body temperature of a mouse. However, as described elsewhere herein, sufficient evidence exists to indicate that utilization of the temperature sensitive gene in combination with a constitutive (i.e., non-regulatable) promotor would be expected not to be compatible with normal development if the promotor was as powerful as, for example, the beta-actin promotor. Thus, other differentiation inhibiting genes can also be used in the present invention, insofar as they are regulatable by a non-constitutive promotor which is inactive in most or all tissues of the normally developing body.

Primary cells used in the work described below to illustrate this invention were cells from the skin, thymus, pancreas, central nervous system, colonic crypts, endothelium, skeletal muscle, and enteric glial cells. However, it is to be understood that the method of the present invention can be used to immortalize virtually any type of cell from the body of an appropriate transgenic animal. Because the particular cells chosen to exemplify the invention herein are from tissues in which extensive cellular characterization has been carried out, it can be confirmed that the cell lines derived by the method of the present invention express properties expected of normal cells. These cell lines thus provide direct verification of the ability of the present method to be used to produce continuous cell lines of a wide variety of cell types from a wide variety of tissues. In addition, some of the work described herein demonstrates directly the utility of the animals in generating cultures in which novel cell types are amenable to study.

Figure 2:
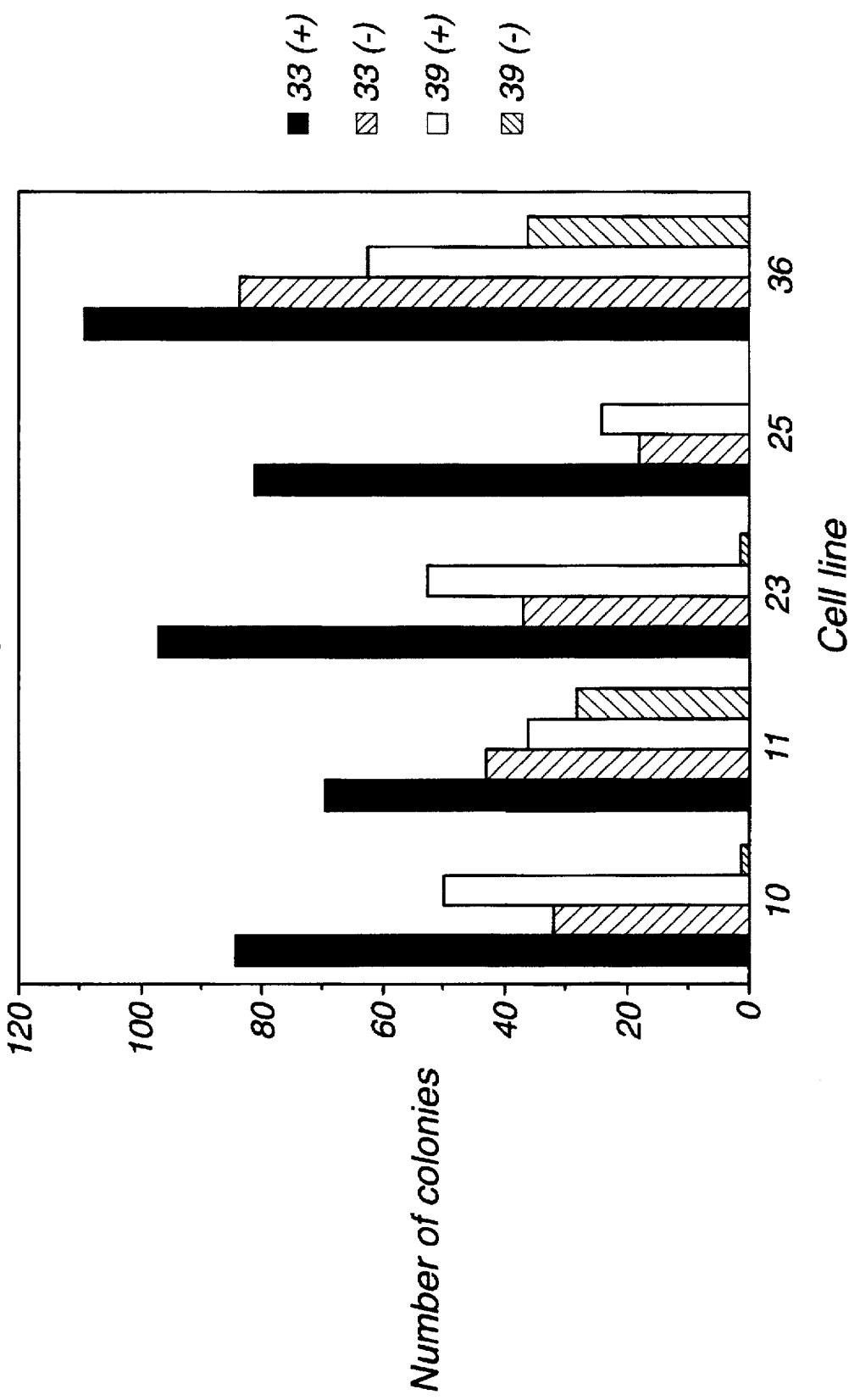
FIG. 2 is a growth analysis diagram demonstrating that control of the biological activity of the SV40tsA58 gene occurs in accordance with the principles of the invention.

The skin was utilized as a principal source of fibroblasts to confirm that the general principles embodies in this invention were correct. Cells from the skin were placed into tissue culture in conditions which activate the promotor used and at temperatures which are permissive for expression of the immortalizing function of TAgts. These cells were grown for various lengths of time before being switched to conditions which did not activate promotor function, which were non-permissive for TAgts function, or both. As shown in FIG. 2 for different transgenic mice, removal of the promotor activating compound (in this case murine gamma interferon) was associated with a reduction in the growth rate of the cells. Growth of cells from most animals was not completely suppressed unless the cells were grown in the absence of gamma interferon and at 39.5° C.; this capacity of cells to continue growing, albeit at a reduced rate, in the absence of gamma interferon seems likely to be due to the low level of constitutive expression of Class I antigens in fibroblasts (Israel A. et al, Nature 322, 743–746). Indeed, it is striking that even the low level of constitutive expression of this promotor which is seen in normal fibroblasts was not associated with the development of any obvious hyperplastic abnormalities of the skin. FIG. 2 also shows that expression of a higher copy number of the gene of interest can be associated with continued slow growth of cells even when cells are grown at 39.5° C. in the absence of interferon (cultures derived from animals 11 and 36 in the work described below). This slow growth is similar to that seen if cells deprived of gamma interferon are grown at 33° C., and is probably due to a breakthrough of activity of the large amounts of T antigen produced (due to the presence of multiple gene copies) prior to its inactivation through degradation at this non-permissive temperature.

The entry of fibroblasts into a non-dividing state when activity of the differentiation inhibiting gene is terminated by gamma interferon withdrawal and growth at 39.5° C. is similar to that observed in previous studies on the effects of immortalization of fibroblasts with TAgts. In these previous studies (in which TAgts expression was controlled with a constitutively active viral LTR and in which retroviral-mediated gene insertion was used to generate cell lines expressing only a single copy of the TAgts gene), cells grown at 33° C. could be grown in tissue culture indefinitely. In contrast, when cells were switched to 39.5° C. they rapidly lost the capacity to undergo further cell division (Jat and Sharp, 1989 Mol.

The entry of conditionally immortalized fibroblasts into a non-dividing state is of particular interest in respect to the way in which this non-dividing state reflects a normal differentiation pathway of fibroblasts. Normal fibroblasts undergo a limited number of divisions before entering a state of senescence in which the cells show normal metabolic function with the exception of being refractory to further cell division (Hayflick L. et al, 1961 Exp. Cell Res. 25, 285, Todaro et al, 1963 J. Cell Biol. 17, 299–313). The phenotype expressed by conditionally immortalized fibroblasts when they are switched from permissive to non-permissive conditions resembles the state of normal senescence so closely as to be indistinguishable. Thus, conditionally immortalized cells can undergo the differentiation events of their normal counterparts when grown in non-permissive conditions.

Two of the cell lines developed from the thymus, as an illustration of this invention, are defined as epithelial cell lines by virtue of expression of cytokeratins. The derivation of an epithelial cell line was of particular interest because of the importance of these cells in human cancer, and the derivation of a thymic epithelial cell line was of further interest due to the putative importance of these cells in the development of the T-lymphocyte populations of the thymus. Cell lines were derived from the thymus because of the tendency of many of the transgenic mice produced to develop thymic hyperplasia. The cell lines derived from this tissue all behaved in a conditional manner in tissue culture, and were growth arrested when growth in the absence of interferon at 39.5° C. The conditionality of these cell lines in vitro indicates that even in this tissue the constitutive levels which occur in vitro are insufficient to cause sufficient levels of TAg to be expressed to be able to interfere with normal processes of differentiation and growth control. Such an observation is consistent with the hypothesis that the generation of thymic hyperplasia in vivo was enhanced by the presence of a hepatitis infection in the mouse colony. Such an infection would cause augmented production of interferon in the thymus, thus driving the levels of T antigen above the threshold of non-effectiveness. These results further support the view that it is necessary to avoid levels of TAgts being inappropriately expressed in every cell in body (rather than just those cells exposed to inducer) as a consequence, in this case of disease in the mouse colony).

A cell line from the central nervous system, as a further illustration of this invention, is of particular interest as a putative precursor for glial tumours and as a demonstration of the potential usefulness of the transgenically derived cell lines as tools for the study of differentiation control. This cell line expresses astrocyte specific antigens when grown in certain tissue culture conditions, but can be induced to express a fibroblast-like phenotype in other tissue culture conditions. The rationale for the characterization of this CNS line as a putative glioma precursor comes from observations that human gliomas can be antigenically divided into two categories: cells which express glial fibrillary acidic protein (GFAP) and are clearly derived from astrocytes, and cells which do not express GFAP but instead express fibronectin (FN). It has been demonstrated that cloning of GFAP-expressing lines can lead to the generation of GFAP-negative cell lines which express fibronectin, thus suggesting that the fibronectin-expressing cells (which do not correlate with any known CNS glial cell) may be traceable back to a CNS lineage. It is potentially relevant to these observations that some experiments indicate that an apparently rare subset of GFAP-positive astrocytes may also express FN (which is not expressed by most astrocytes). The cell line described herein can be switched from a GFAP-positive phenotype to a FN-positive GFAP-negative phenotype by growth in fetal calf corum. The ability to manipulate the differentiation of this cell provides a suitable assay system for use in the purification of the specific molecular signals which induce differentiation along the FN-positive GFAP-negative pathway.

A further cell line prepared by the method of the present invention was derived from the pancreas. A small percentage of the cells in this line spontaneously express insulin in all conditions of growth, and some cells of the line also can be labeled with a monoclonal antibody (A2B5) thought to label islet cells of the pancreas. It is not yet known if the variable expression of these markers within the cell line is due to failure to create appropriate differentiation-inducing microenviornments in the tissue culture conditions.

Other matters specifically illustrated by the work described herein (and relevant aspects of the invention) are specifically referred to in the respective Examples hereinafter.

The following non-liming Examples are given to demonstrate and illustrate the principles of the invention.

As used in what follows, "mouse x" means the xth mouse from the first described experiment.

EXAMPLE 1

Construction of pH-2KbtsA58 Genetic Construct

Figure 1:
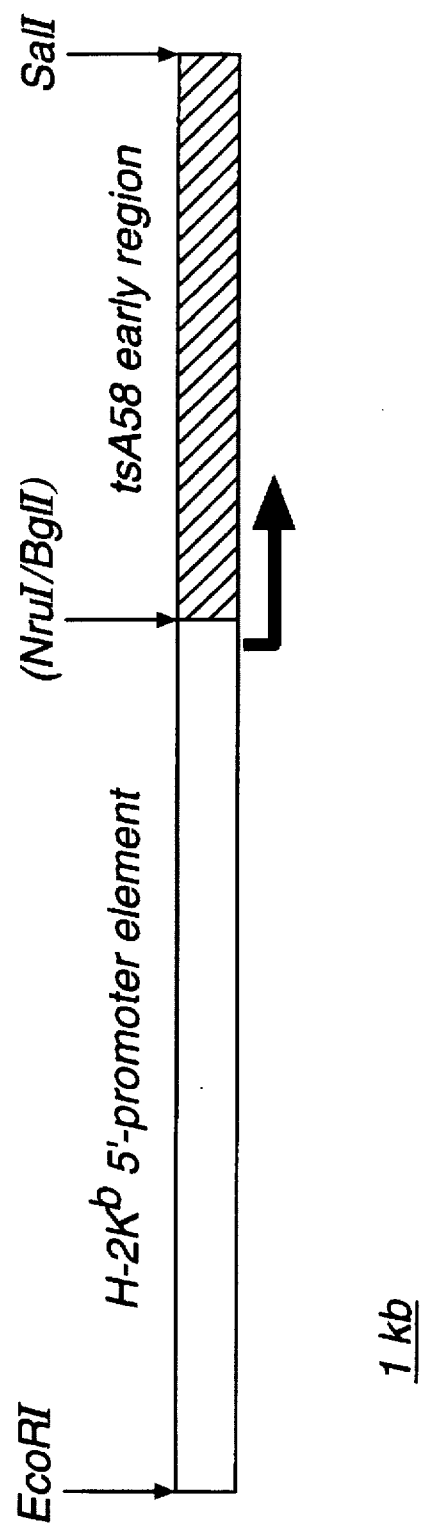
FIG. 1 is a schematic representation of genetic construct H-2K$^b$tsA58, referred to in the Examples hereinafter.

Recombinant pH-2KbtsA58 (see FIG. 1) was constructed by attaching the 5'-promotor element of the H-2Kb gene to the early region coding sequences from the SV40 mutant tsA58. The promotor fragment was isolated as the approximately 4.2kb EcoRl-NruI fragment from plasmid pH-2Kb (which was provided by Dr. Andrew Mellor, MRC London). This plasmid was constructed by cloning the EcoRl fragment which encompasses the genomic sequences encoding the H-2Kb gene from the cosmid 88H8 (Weiss et al, Nature 1983, 301 671–674) into plasmid pBR327. The tsA58 DNA was described by Tegtmeyer 1975 J. Virology 16, 168–178. In the present Examples, the SV40 tsA58 coding sequences were isolated as an approximately 2.6kb BglI-BamHI fragment from pUCSV40tsA58 which was provided by Dr. Harmut Land (of the Imperial Cancer Research Fund, London). This plasmid was constructed by inserting the Kpnl (nucleotide.294) to the BamHI (nucleotide 2533) fragment from tsA58 DNA, which encodes the T antigen coding sequences, into the Kpnl and BamHI sites of pUCl9. The BglI site was blunt-ended using the Klenow fragment of DNA polymerase I. The two fragments were ligated with an equimolar amount of $p^{uc19}$ which had been digested with EcoRl and BamHI. The ligated products were transformed into JS4, a recA$^-$ derivative of $E.\ coli$ MC1061 (Casadaban and Cohen 1980 J. Mol. Biol. 138, 179–207; Sedivy et al 1987 Cell 50, 379–389) and ampicillin colonies isolated. DNA minipreps were prepared from isolated colonies and analysed by digestion with various restriction endonucleases to determine if the promotor fragment had been successfully fused to the T antigen coding sequences.

Production of Transgenic Mice containing H2K$^b$-Tagts fusions

The above H-2K$^b$-TAgtsA58 plasmids were digested with EcoRl and SalI to prepare DNA fragments which were free of vector sequences. These DNA fragments were isolated on agarose gels and injected into male pronuclei of fertilized one-cell mouse eggs at a concentration of 1–2 ug/ml DNA in TE buffer (10 mM Tris, pH 7.5, 0.2 mM EDTA). The eggs which survived micro-injection were transferred to pseudopregnant females as described in Wagner et al (1981) P.N.A.S. 78, 5016. The eggs were derived from a CBA× C57BL/10 mating. The mice were obtained from the MRC breeding colonies, and were housed in an environmentally controlled facility maintained on a 10 hour dark:14 hour light cycle. The eggs in the foster females were allowed to develop to term.

Analysis of Transgenic Mice

At 7–14 days of age, each pup was analyzed to determine if it carried the transgene. DNA prepared from a small section of tail was initially analyzed on a slot blot. Genomic DNA was isolated from 0.1– 0.15 cm sections of tail by the method described in Sambrook et al "Molecular Cloning" (Cold Spring Harbor 1989). The resulting nucleic acid pellet was washed once in 80% ethanol, dried and resuspended in 200 ul of 10.0 mM Tris, pH 7.4, 1 mM EDTA. The presence of the construct was determined by hybridizing the filter with a $^{32}$P-labeled fragment specific for the SV40 large T antigen. The probe was prepared by the random priming method of Feinberg & Vogelstein. The integrity of the TAg gene was verified by Southern blot analysis by digesting 10 ug of tail DNA with BamHI. The digested DNA was fractionated on an 0.8% agarose gel, transferred to Zeta Bind™ (Biorad) and hybridized with an SV40 specific probe using published methods (as described in Sambrook et al). Blots were probed with a $^{32}$p labeled probe for the TAg gene. All manipulations were carried out using either the manufacturers recommended conditions or by standard protocols as described in Sambrook et al, supra. The slot blot indicated that 34 out of 88 mice carried the chimeric gene. The number of copies of this fusion gene present in the mice DNA varied from 1 up to 15 copies per cell.

Animals containing the H-2K$^b$-TAgtsA58 fusion gene developed normally with the exception of the development of a thymic hyperplasia. There appeared to be a distinct correlation between the levels of TAg mRNA expressed and the rapidity of onset of thymic hyperplasia. That the thymic enlargement seen was not the result of neoplastic transformation was indicated by the fact that both lobes of the thymus were equally enlarged, and that injection of even as many as $10^7$ thymus-derived cells into native recipient mice (either subcutaneously or intraperitoneally) in no case caused tumours in the host mice. In addition, as described below, almost all stromal cell lines derived from these enlarged thymi appeared to be conditional for growth in culture. The thymic hyperplasia may have been in part due to the presence of an infection of mouse hepatitis virus in the animal colony, which would be expected to cause interferon production in infected animals. Therefore the hepatitis infection is likely to have been aggravated by the already high levels of endogenous Class I antigen expression in thymic tissue, resulting in expression of TAgtsA58 at a higher level in vivo than would be the case for other tissues of the body. One of the strains of mice expressing only one copy of the hybrid gene took longer (6 months for heterozygotes and 3–4 months for homozygotes) for the hyperplasia to occur.

As described below for cells grown in tissue culture, in cases where large amounts of TAgtsA58 are transcribed (in association with the presence of multiple genetic copies in the DNA of the mice), it appears that marginal effects of TAgtsA58 on growth promotion do occur even at the permissive temperature. In one of the mice in which only one copy of TAgtsA58 was present in the genome thymic hyperplasia developed only after several months, and mice were to breed normally and effectively, transmitting the H2K$^b$-TAgtsA58 fusion to the offspring.

Analysis of Fibroblasts from H2K$^b$-TAgtsA58 Transgenic Mice

The following demonstrates the importance of screening for mice which show low levels of transgene expression in vivo in order that the mice function in accordance with the principles of the invention. As already indicated, this method of selection is antithetical to the standard methods of transgenic animal selection, in which high levels of in vivo transgene expression are sought so as to have a maximal probability of disrupting normal in vivo development.

To demonstrate that the expression of H2K$^b$-TAgtsA58 in tissues of transgenic mice allowed the generation of cell lines which were conditionally immortalized, the growth of skin fibroblasts was examined. Fibroblasts were derived from 5 different mice by first sacrificing the mouse by cervical dislocation, sterilizing the skin and fur with ethanol, shaving off the fur, and dissecting several square cm of skin. This skin was then finely minced with a sterile scalpel and digested in 500 units per ml collagenase for 2 h at 37° C. in Leibovitz's L-15 medium. Trypsin was then added to a final concentration of 3000 units per ml, and tissue was incubated for a further 15 min at 37° C. Following this incubation, the enzymatic digestion was terminated by the addition of a solution of soy bean trypsin inhibitor (1000 units per ml) and DNAse (15 units per ml) also prepared in L-15. Tissue was then brought to a volume of 5 ml and was gently triturated up and down in a sterile plastic pipette a total of 20 times. Undissociated chunks of tissue were allowed to settle out and the cells contained in the supernatant were first washed by centrifugation and then resuspended in Dulbecco's Modified Eagle's Medium containing 2 mM glutamine and 10% fetal calf serum and 100 U/ml of recombinant murine gamma interferon. In all cases in which cells were derived from mice carrying the H2K$^b$-TagtsA58 the cultures prepared in this way grew effectively in tissue culture flasks. Cells were also prepared and grown in identical ways from identically aged normal controls and as, discussed below, the cells from normal mice succumbed to senensence after short periods of time. The cultures prepared from the H2K$^b$-TAgtsA58 fusion transgenic mice were grown at 33° C. in the presence of 100 U/ml of gamma interferon for between 8 and 12 weeks before being tested for the conditionality of their growth. Long before this time all cells derived from mice which did not harbour the H2K$^b$-TAgtsA58 fusion construct had undergone crisis and stopped dividing, as expected for non-immortalized fibroblasts. In all fibroblast lines derived from the H2K$^b$-TAgtsA58 fusion transgenic mice, the placement of these cells in non-permissive conditions inhibited cell growth. FIG. 2 shows the results of a colony-forming assay, in which 1000 cells were plated in a 6 cm dish in DMEM+FCS lacking interferon for 24 h, and then were switched into medium which either contained or did not contain 100 U/ml of murine gamma interferon and allowed to grow for 14 days at either 33° C. or 39.5° C., during which time medium was changed twice-weekly. The 24 h preplating in normal medium insures that the initial plating efficiency was the same in all cultures. After 14 days the cultures were stained with 2% methylene blue, 50% ethanol:water and the number of colonies obtained was counted. As shown in FIG. 2, the growth of cells in fully permissive conditions (i.e., 33° C., 100 U/ml of murine gamma interferon) was greater than in any of the non permissive conditions.

Detailed analysis of skin fibroblast cultures for conditionality of growth revealed 3 families of cultures, depending upon the ability of cells to grow in fully permissive, semipermissive and nonpermissive conditions; permissive conditions were defined for these purposes as growth at 33° C. in the presence of IFN-gamma, semipermissive conditions included either growth at 33° C. in the absence of IFN-gamma or 39.5° C. in the presence of IFN-gamma and nonpermissive conditions were growth at 39.5° C. in the absence of IFN-gamma.

In the first family of cultures, growth was fully conditional and only occurred in permissive conditions. If cells were grown at 39.5° C. and/or were grown in the absence of IFN-gamma, cell division did not occur either in standard growth assays or in colony forming assays. These fibroblasts thus behaved as expected from previous studies in which rat embryo fibroblasts were conditionally immortalized with tsA58TAg by retroviral infection (Jat & Sharp, 1989, Mol. Cell. Biol., 9:3093–3096). In these previous studies, it has been shown that fibroblasts which are conditionally immortalized using retroviral-mediated gene insertion to create cell lines which express tsA58TAg will continue to proliferate only if maintained in permissive conditions. Upon temperature shift to non-permissive conditions, fibroblasts rapidly express the senescent phenotype expressed by normal fibroblasts which have been grown for extended periods in vitro. All cultures derived from different individuals within the H2K$^b$-TAgtsA58 strain of mice yielded identical results.

In a second family of cultures, optimal growth was obtained in fully permissive conditions, a lesser degree of growth was seen in semipermissive conditions and no growth occurred in nonpermissive conditions. In the third family, cell growth did not completely cease even when cells were grown under nonpermissive conditions, although the best growth was seen in fully permissive conditions and the slowest growth occurred at the fully nonpermissive conditions.

The conditionality of growth observed in the fibroblasts derived from transgenic animals was correlated with the levels of tsA58TAg expressed by these cells. In all cultures, the level of tsA58TAg was reduced by temperature shiftup and/or by removal of IFN-gamma. Interestingly, when the most conditional cultures (those derived from progeny of mouse H2ts6) were grown at 33° C. in the absence of IFN-gamma, a condition where these cells did not grow, low levels of TAg could still be detected. This observation is discussed in further detail in the next Example.

To determine whether cell lines which were conditionally immortal could be rendered fully immortal by the introduction of a constitutively active differentiation inhibiting gene, some of the fibroblasts isolated from the H2ts6 mice were infected with a retrovirus which expressed a wild-type SV40 T antigen and the neomycin resistance gene (Jat & Sharp, J. Virol., 1986, 59:746–750). Cells which were successfully infected were selected by growth in the G418 antibiotic. When these cells were then switched to non-permissive conditions, the cells continued to grow. These experiments thus demonstrate that a cell line can be converted from a conditional to a non-conditional growth state if it is considered desirable to do so.

Analysis of Cell Lines from H2K$^b$-TAgtsA58 Transgenic Mice

Analysis of thymic cell line (1) This work demonstrates that even in the single instance found where the genetic construct used does disrupt normal development, the cell types which have undergone hyperplastic expansion in vivo remain conditional in their in vitro growth.

(2) This work further demonstrates that thymic epithelial cells derived from H2ts6 mice express the family of intermediate filament proteins normally expressed by these cells in vivo, thus making these cells a potentially suitable source for the purification of proteins expressed in their normal counterparts.

(3) This work also demonstrates that the thymic epithelial cell lines derived from H2ts6 mice have the ability to rosette T-lymphocytes, thus making them a suitable cell-type for the study and potential biochemical dissection of a normal cellular interaction.

Because of the development of thymic hyperplasia in many of the H2K$^b$-TAgtsA58 fusion transgenic mice it was of importance to characterize the growth of thymic derived cells. To this end, thymic tissue was prepared for culture in the same manner as for fibroblasts, except that the periods for which enzymes were added were limited to a total of 15 min of collagenase together with a further 15 min in the additional presence of trypsin. These cells were then grown as were the skin fibroblasts until confluent flasks were obtained, after which clonal cell lines were isolated by limited diluation single cell cloning.

The cell lines isolated from the thymuses of the H2K$^b$-TAgtsA58 fusion transgenic mice were conditional in their growth, and were growth arrested when grown in the absence of interferon at 39.5° C. The conditionality of these cell lines in vitro indicates that even in this tissue the endogenous levels of Class I antigen expression are insufficient to cause sufficient levels of T antigen to be expressed to be able to interfere with normal processes of differentiation and growth control. Such an observation is consistent with the hypothesis that the reason for the generation of thymic hyperplasia in vivo was probably due to the presence of a hepatitis infection in the mouse colony. Such an infection would cause augmented production of interferon in the thymus, thus driving the levels of T antigen above the threshold of non-effectiveness. These results further support the importance of the use of an inducible, non-constitutive promotor, as a potent constitutive promotor would cause levels of TAgts to be inappropriately expressed in every cell in the body rather than just those cells exposed to inducer as a consequence, in this case, of disease in the mouse colony.

Two of the cell lines derived from the thymus were characterized antigenically, and were found to express cytokeratins by staining the cells with the LE61 pan-anti keratin monoclonal antibody. As keratins are specifically expressed in epithelial cell populations, the labelling of these cells with the LE61 antibody indicates that these cells are thymic epithelial cells.

The cytokeratin positive thymic epithelial cell lines discussed above specifically bound T-lymphocytes, as detected in a standard rosetting assay. Stromal cells were mixed with unfractionated freshly isolated thymocytes from nontransgenic BALB/c mice in a ratio of 1:12. Cells were kept in a small volume (200 microliters) and incubated on ice for one hour. The mixture was then centrifuged at 200 g for 5 minutes, the pellet gently resuspended in 1 ml of PBS and the number of rosettes was counted using a haemocytometer, with 3 or more thymocytes attached to a stromal cell counting as a rosette. In this assay, the cytokeratin+thymic epithelial cell lines efficiently formed rosettes with thymocytes.

Analysis of a putative glioma precursor cell

To derive cell lines of the central nervous system, cells were dissociated from the cerebral cortices of mouse 11 by the methods described in Noble et al (1984, J. Neurosci. 4, 1892–1903). The mouse was 3 weeks old at the time of dissection. Cells were grown in chemically-defined medium (Bottenstein and Sato, 1979, Proc. Natl. Acad. Sci. U.S.A. 76, 514–517) in the presence of 10 ng/ml of platelet-derived growth factor [BB homodimer (supplied by British Biotechnology) and 10 ng/ml PDGF AA homodimer (supplied by Chiron Corporation)] and 10 ng/ml of basic fibroblast growth factor (supplied by Boehringer-Mannheim). Cells were grown through an initial passaging and then cloned by limiting dilution. Ten clones were isolated and characterized for antigen expression. Of these, 1 clone consisted of cells which all expressed glial fibrillary acidic protein (GFAP), a cytoskeletal protein specifically expressed by astrocytes in the CNS (Bignami, et al, 1972 Brain Res 43, 429–435). GFAP expression was analyzed using an anti-GFAP antiserum purchased from Dakopatts Ltd and appropriate fluorescent second layer antibodies (purchased from Southern Biotechnology).

To examine the differentiation potential of the GFAP-expressing clone of cells, cells were replated on poly-L-lysine coated glass coverslips and treated with a variety of different substances to induce differentiation. Of particular interest were the effects of fetal calf serum, which induced cells to develop a GFAP– phenotype. The GFAP– cells did express the extracellular matrix protein fibronectin (FN), which has been reported as being expressed on only some poorly defined astrocytic subpopulations among the CNS glial cells. Although the parental cell line expressed both GFAP and FN, some experiments have suggested that in the absence of serum this parental cell can take on a GFAP+FN– phenotype.

The isolation of a cell with the capacity to be regulated between a GFAP+ phenotype and a GFAP–FN+ phenotype is of exciting interest in light of the results of recent studies on antigen expression in human gliomas. Although morphological classification of human gliomas has generally assumed that these cells share a close lineage relationship with the normal glial cells of the CNS, extensive antigenic analysis of cells derived from gliomas has not been in agreement with the morphological categorization of these tumours (Kennedy et al 1987 Neuropath Appl. Neurobiol 13, 327–347). Most importantly, studies thus far have indicated that gliomas can be slotted into one of two antigenic categories, the first being a GFAP+ phenotype and the second being a GFAP–FN+ phenotype. In work by Kennedy et al, the GFAP–FN+ glioma phenotype was found to occur in almost 90% of cell cultures derived from gliomas. The origin of these cells remains unclear, although it has been shown that clones derived from a GFAP+ glioma may be GFAP– and FN+ (Westphal et al, 1988, Cancer Research 48, 731–740).

The results on human gliomas raise the striking possibility that there exists within the nervous system a precursor cell with the possibility of differentiating along both astrocytic (GFAP+) and non-glial (GFAP–FN+) pathways. The cell we have isolated represents the first time such a cell has been clearly isolated from brain in a manner that allows rigorous examination of this possibility. The congruence between the many studies on antigen expression in glioma cells and the antigenic phenotypes which can be expressed by the cell isolated from mouse 11 suggests clearly that this cell line is a candidate for being a glioma precursor cell.

Analysis of pancreatic cells

Pancreatic cells isolated from the pancreas of mouse 11 in the same manner as cortical cells, and grown and cloned in the same manner as cortical cells, have undergone preliminary characterization in tissue culture. A small proportion of cells in the most closely examined clone express insulin (as recognized by anti-insulin antibodies purchased from ICN) and can be labelled with the monoclonal antibody A2B5 (hybridoma cell line obtained from Dr. Marshall Nirenberg of the National Institute of Health, USA), both of which are markers for pancreatic islet cells (Eisenbarth et al, Proc. Natl. Acad. Sci. U.S.A., 79, 5066–5070).

It is retrospectively unfortunate that both the cortical and pancreatic clones were isolated from mouse 11, which turned out from much later analysis to have been one of the least conditional of the transgenic mice. Preliminary results do however indicate that the cortical and pancreatic cells may be more conditional than fibroblasts. More importantly, neither the brain nor pancreas of mouse 11 showed any evidence of gross developmental abnormalities, indicating that the levels of TAgtsA58 which may have been expressed in these cells was insufficient to interfere with in vivo differentiation. Alternatively, it may be that placement of these cells in tissue culture conditions caused them to express higher levels of Class I antigen then would be the case in vivo.

One of the transgenic mice created with the H2K$^b$tsA58 construct (Mouse No. 6) has bred successfully to produce several litters, all of which have pups which carry the original genotype. In all the Examples that follow, the transgenic animals used were heterozygous progeny of what is termed the H2ts6 strain (Mouse No. 6).

EXAMPLE 2

Cells were prepared from the heart of one of the offspring of mouse 6 by the same methods by which fibroblasts were prepared from the skin of other mice. The mouse from which the heart tissue was prepared (called "daughter of 6") exhibited no obvious abnormalities in organ size upon dissection.

Figure 3:
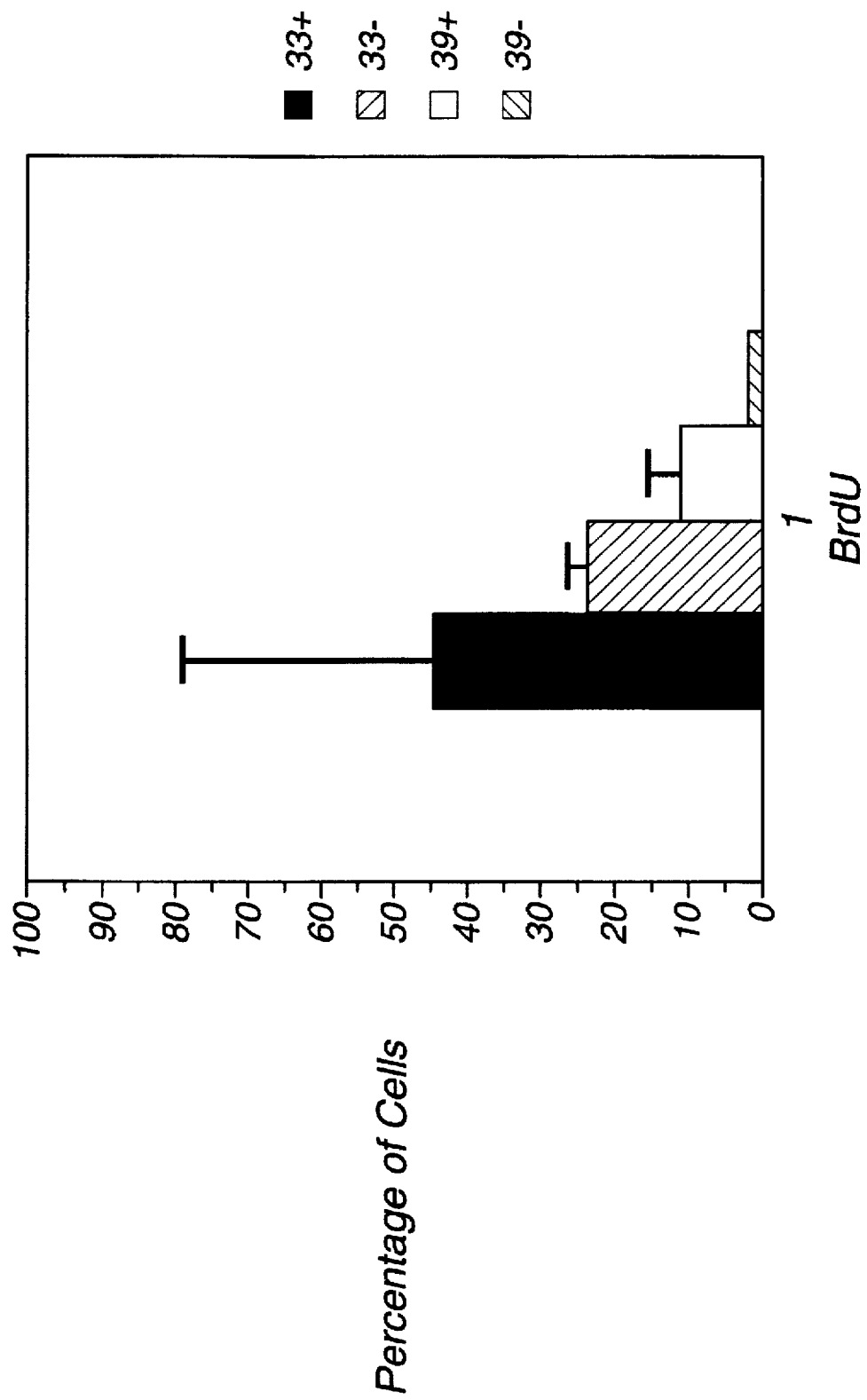
FIG. 3 shows DNA synthesis under various conditions for heart fibroblast cells from a mouse in accordance with the invention and carrying the genetic construct of FIG. 1.

Cells from daughter of 6 (which were recognised as being likely heart-derived fibroblasts) were grown for 4 weeks at 33° C. in the presence of recombinant murine gamma interferon. For experimental analysis, cells were plated onto poly-L-lysine coated glass cover slips at 33° C. in DMEM+ 10% fetal calf serum overnight. On the following day the cells were switched to growth at 33° C. or 39.5° C. in the presence or absence of gamma interferon. After 3 days of growth in permissive or non-permissive conditions, bromodeoxyuridine was added for 24 h and cells were then fixed (by the protocol supplied by Becton Dickinson) and stained with anti-bromodeoxyuridine antibodies (purchased from Becton Dickinson), followed by a rhodamine conjugated second antibody (purchased from Southern Biotechnology) to label nuclei of cells which had engaged in DNA synthesis during the previous 24 h. As shown in FIG. 3, cells grown at 33° C. in the presence of interferon had a 20-fold greater synthesis of DNA during the labelling period than cells grown at 39.5° C. in the absence of interferon. Cells grown in semi-permissive conditions showed intermediate levels of DNA synthesis fully compatible with survival.

EXAMPLE 3

(1) The following work demonstrates the principle that cells derived from H2ts6 mice are conditionally immortal, and undergo a normal pathways of terminal differentiation when switched from permissive to non-permissive conditions.

(2) This work further demonstrates that it is possible to express subfunctional levels of oncogene product, thus confirming the principle that it is possible to express levels of oncogene product which do not interfere with normal developmental pathways.

(3) Moreover, this work also demonstrates the need for fine regulation of oncogene activity in order to keep activity below a level which would interfere with normal development.

Cultures of skin fibroblasts from H2ts6 mice were prepared as described in Example 1, and displayed the conditionally immortalized phenotype discussed in detail in the previous Example.

Western blot analysis of expression of T antigen in cultures of fibroblasts derived from H2ts6 mice showed a relatively low level of T antigen expression at 33° C. in the presence or absence of IFN-gamma although expression was clearly higher in the presence of IFN-gamma. This observation indicated that is might be possible to observe dramatic alterations in cell growth as a result of small changes in the level of this gene product. To test this possibility, a dose-response analysis was effected in which cell growth and colony formation were titred against the concentration of IFN-gamma.

Fibroblasts derived from progeny of H2ts6 mice showed promotion of cell growth by levels of IFN-gamma as low as 1 U/ml. Analysis by colony formation and by cell number analysis showed that addition of 100 U/ml of IFN-gamma to these cultures only increased the frequency of colony formation by 3.5 fold in comparison with that seen in the presence of 1 U/ml, and was only 40% increased over that achieved with application of 10 U/ml. The difference in TAg levels at the different doses of IFN-gamma was not large, with 1 U/ml causing a 2.5-fold increase over basal levels and 100 U/ml causing approximately a 6-fold increase over basal levels.

EXAMPLE 4

Generation of astrocyte cell lines

This Example demonstrates four aspects of the use of animals of the invention:

(1) Astrocyte cell lines, representing a defined differentiated cell type, were generated from the central nervous system, a tissue where the endogeneous level of class 1 antigen expression is essentially non-existent and where no mRNA production in vivo can be detected. Thus, it is demonstrated that transcription of the oncogene construct in vivo is not a prior requisite to the generation of a cell line.

(2) The astrocyte cell lines express the normal cell-type specific marker associated with this cell type, thus demonstrating the potential usefulness of cells derived from the H2ts6 mice as a source of purification of a cell-type specific protein.

(3) The astrocyte cell lines produce a mitogenic activity known to be expressed by the normal counterparts of the cells, thus indicating that the astrocyte cell lines derived from the H2ts6 mice are capable of promoting the division of another cell type, and thus represent a potential source for the purification of the mitogenic factor.

(4) Finally, the astrocyte cell lines were generated by first growing brain cells in normal (non-permissive) tissue culture conditions, followed by purification of the cell-type of interest, followed by growth of the cells of interest in permissive conditions. This thus demonstrates that the turning on of oncogene function can occur after cells have been grown in tissue culture for a period of time, thus demonstrating that cells need not even be conditionally immortalized at the time of initial dissection.

Cultures of cortical astrocytes were prepared by standard procedures (Noble et al., 1984, J. Neurosci., 4:1892–1903; Noble & Murray, 1984, EMBO J. 3:2243–2247). Briefly, cortices from newborn H2ts6 mice were dissociated into single cells by enzymatic digestion of tissue with 0.25% collagenase in L-15 medium and an equal volume of 0.25% trypsin. Cultures were grown at 37° C. in DMEM containing 10% fetal calf serum, 2 mM glutamine and 25 microgram/ml of gentamicin. After 7–10 days cultures were placed on a rotary platform overnight at 37° C., and were rotated at speeds just below those which would cause foaming of the medium (i.e., about 60–75 rpm). As described previously (Noble et al., 1984), this procedure produces cultures which are 95% pure astrocytes, as judged by the expression of the astrocyte-specific cytoskeletal protein GFAP (glial fibrillary acidic protein) in 95% of these cells.

After cultures of astrocytes were enriched to >95% purity, clonal cell lines were generated by first shifting cells to 33° C. in the presence of gamma-interferon. Cells were then infected with a retrovirus which harbours genes for bacterial beta-galactosidase and a neomycin resistance gene, using the standard infection protocol described for the use of this virus (Price et al., Proc. Natl. Acad. Sci., USA, 1987, 85:156–160). One day after infection, cells were removed from the flask by incubation with 0.25% trypsin (see Noble et al., 1984, supra) and replated in medium containing the G418 antibiotic. Resistant clones of cells emerged from the selection condition, and 10 random clones were selected for further study. Clonal cell lines were readily generated in this manner and 7 of the 10 cell lines constitutively expressed glial fibrillary acidic protein (GFAP), a specific marker for astrocytes in the CNS.

To examine the ability of the astrocyte cell lines to produce mitogenic activity normally associated with these cells, oligodendrocyte-type-2 astrocyte (O-2A) progenitor cells were plated from the optic nerves of 7 day old rats onto the astrocyte monolayers. In previous experiments (Noble & Murray, 1984) it has been shown that astrocytes, but not meningeal cells or fibroblasts, were able to stimulate division of O-2A progenitors in vitro, and that the O-2A progenitors stimulated to divide by astrocyte conditioned medium expressed a particular bipolar morphology which is only seen when these progenitors are grown in the presence of astrocyte monolayers, astrocyte-conditioned medium or platelet-derived growth factor (the mitogen produced by these astrocyte monolayers). O-2A progenitors grown on monolayers of clonal astrocyte cell lines derived from the H2ts6 strain of transgenic mice were indistinguishable from those grown on nontransgenic astrocytes in their division and expression of the expected bipolar morphology.

EXAMPLE 5

Glial precursors of the CNS

This Example demonstrates that:

(1) It is possible directly to immortalize cells from the central nervous system with the characteristics of novel precursor cells by growth of cells in permissive conditions, and that the cells grown in this way display the blockade of differentiation normally associated with expression of nuclear oncogenes. Thus, this Example further demonstrates the ability to generate immortalized cell cultures from a tissue of the body in which there is no detectable in vivo expression of the transgene.

(2) Cell division requires the presence of appropriate growth factors, thus indicating the potential usefulness of cells derived from the H2ts6 mice as assay systems useful in growth factor purification.

(3) Precursor cells derived from the H2ts6 mice can be induced to undergo differentiation by switching cells from permissive to non-permissive conditions, thus demonstrating the potential usefulness of these cells in allowing the growth of novel precursor cells.

(4) Precursor cells grown according to the methods of the invention also retain the capacity to undergo normal differentiation when grown in permissive conditions if cells are exposed to either defined molecular factors or to medium conditioned from a cellular source. This Example thus further demonstrates the potential suitability of cells derived from the H2ts6 mice for use in assay systems which would enable the purification of factors which induce cellular differentiation.

Cortical cells were dissociated as described in Example 3, except that cells were derived from embryonic day 18 mice and were grown in chemically defined medium (ingredients as described in Raff et al., 1983, Nature, 303:390–396) containing 10 ng/ml of the AA-homodimer of platelet-derived growth factor (Chiron Corporation), 5 ng/ml of basic fibroblast growth factor (Chiron Corporation) and 20 U/ml IFN-gamma. Cells could be passaged readily, and passaged cells maintained in the indicated conditions showed no evidence of differentiation into defined glial cell types. Cultures contained bipolar cells which could be labeled with the A2B5 monoclonal antibody (Eisenbarth et al., 1979, Proc. Natl. Acad. Sci., U.S.A. 76:4913–4917), and looked like the O-2A progenitors which have been described in cultures of optic nerve cells (e.g., Raff et al., Nature, 1983, 303:390–396; Noble & Murray, 1984, EMBO J., 3:2243–2247). Cultures also contained a separate group of novel cells which were labeled by antibodies against the vimentin intermediate filament (antibodies from Dako-Patts, Ltd.) and with antibodies against SSEA-1 (stage-specific embryonic antigen-1, described in Gooi et al., Nature, 1981, 292:156–158). These novel cells expressed a very primitive morphology and consisted of small round cells with few processes or cytoplasmic extensions. In previous experiments with cultures prepared from cortices of embryonic rats, similar cells have been seen which invariably differentiated into astrocytes or oligodendrocytes upon passaging, regardless of the medium into which passaged cells were replated. In contrast, cells derived from the H2ts6 mice maintained in the described growth conditions could readily be repeatedly passaged without undergoing differentiation.

The cortical cells derived from cortices of H2ts6 mice could be induced to differentiate by several in vitro manipulations. In all cases, cultures produced oligodendrocytes (which seemed to be derived from the A2B5+ cells, as the oligodendrocytes were A2B5+SSEA-1$^-$) and astrocytes (which appeared to be derived from the SSEA-1$^+$·cells as the astrocytes were frequently SSEA-1$^+$ but always A2B5$^-$). In both cases cellular morphology altered dramatically. Oligodendrocytes expressed their normal multipolar appearance and could be labelled by monoclonal antibodies against galactocerebroside (Ranscht et al., 1982, Proc. Natl. Acad. Sci., USA., 79:2709–2713). Cellular morphology also changed dramatically in the case of astrocytic differentiation, and the small primitive-looking SSEA-1$^+$ cells were replaced by SSEA-1$^+$ cells with large cell bodies and broad membrane expanses. The cells undergoing astrocytic differentiation not only looked like astrocytes, but also expressed GFAP.

First, removal of PDGF and FGF resulted in differentiation and cell death, thus demonstrating that the oncogene-expressing cells required the continuous presence of appropriate growth factors in order to continue growing. Second, cells which were maintained in the growth medium and in the presence of growth factors also differentiated if IFN-gamma was removed from the medium (thus turning off the TAgts expression). This result demonstrates that expression of TAgts is necessary to prevent differentiation even if cells are grown in conditions which allow oncogene-expressing cells to continue growing in a non-differentiated state. Third, cells grown in the presence of PDGF and bFGF in fully permissive conditions (i.e., 33° C.,+IFN-gamma) could be induced to differentiate if exposed to medium conditioned by purified cortical astrocytes (prepared as in Noble et al., 1984, J. Neurosci. 4:1892–1903), thus demonstrating the potential suitability of the H2ts6 precursor cells for use in assay systems for the detection and purification of differentiation inducing agents. Fourth, cells grown in the presence of PDGF and bFGF in fully permissive conditions should be induced to differentiate by exposure to 10 ng/ml transforming growth factor-beta (British Biotechnology) or by exposure to 2 ng/ml of ciliary neurotrophic factor (Synergen), thus indicating the responsiveness of the precursor cells to defined differentiation inducing agents known to be present in the central nervous system, thus further indicating the potential suitability of the H2ts6 precursor cells for use in assay systems for the detection and purification of differentiation inducing agents.

EXAMPLE 6

Endothelial Cells (1) This Example demonstrates that the H2ts6 mice can be used to generate cell lines of endothelial origin.

(2) This Example further demonstrates that the endothelial cell cultures generated from the H2ts6 mice secrete a novel differentiation-promoting activity known to be secreted by normal endothelial cells. Thus, this Example further demonstrates the potential usefulness of cell lines derived from the H2ts6 as a source material which would allow subsequent purification of a molecule expressing a unique biological activity.

Endothelial cell colonies were prepared as follows: Two adult mice (2–3 months of age) were decapitated under $CO_2$ coma. The brains were washed in Leibowitz L-15 medium containing 25 microgram/ml of gentamicin and then placed in fresh L-15. Each brain was placed in a 30 mm petri dish containing a few mls of L-15. The cerebellum and other white matter tracts (corpus callosum, optic bulb) were removed by dissection. The meningeal sheath was removed without leaving any traces. The remaining grey matter was chopped finely with a sterile scalpel blade and then forced through a gauge 19 needle once and incubated in 0.1% collagenase:dipase (BCL) in L-15 for 60 min at 30° C. The tissue was spun at 1000 g for 10 min at 4° C. and the supernatant discarded. Twenty ml of 25% BSA in L-15 were added and mixed thoroughly but without frothing and spun at 2000 g for 20 min. The floating layer of tissue together with the supernatant was removed with care without disturbing the small pellet. The supernatant and the tissue were mixed and spun again at 2000 g for 20 min. This time the tissue layer and supernatant were discarded and the two pellets were suspended in 10 ml of 0.5% BSA in L-15 and spun at 1000 g for 10 min at 4° C. to wash the pellets. The pellet was suspended in 0.1% collagenase:dispase (in L-15) and incubated at 30° C. for two hours. After the incubation, DNAse was added to a final concentration of 10 microgram/ml and the resulting capillary-containing tissues were spun at 1000 g for 10 min at 4° C. The pellet was again suspended gently in 1 ml of Ca—Mg-free DMEM and layered onto a 10 ml Percoll gradient and spun at 1000 g for 10 min at 4° C. (A linear gradient of 50% Percoll (Pharmacia) in Ca—Mg-free PBS was prepared in advance by mixing 5 parts isotonic Percoll [9 parts Percoll with 1 part 10X Ca—Mg-free PBS] with 5 parts of 1X PBS and spinning at 26,000 g for one hour.) The top half of the tube contained cellular debris and single cells. The bottom half contained red blood cells seen as a red ring, and just above this ring were the intact capillaries. This layer was removed carefully and suspended in 15 ml of L-15 and spun at 1000 g for 20 min at 4° C. The supernatant was discarded and the capillaries suspended gently in growth media (DMEM with 4.5 g/L glucose supplemented with 2 mM glutamine, 20% plasma derived serum as described by Vogel et al. (Proc. Natl. Acad. Sci., 1978, 75:2810–2814), 10 IU/ml Heparin (Sigma), 5 ng/ml basic FGF (Chiron Corporation) and 20 U/ml of IFN-gamma. The capillaries were plated onto Vitrogen (Flow Lab) coated 96 well plates at 50% occupancy and incubated at 7.5% $CO_2$. The media was changed after three days and then every two days thereafter. Wells with single capillaries were tagged at day 3 and followed to confluence. Endothelial cells arising from these capillaries grew as colonies with tight boundaries. These cells could then be passaged by gently trypsinizing cells (0.025% trypsin in Ca—Mg free DMEM containing 2 mM EDTA, 3 min at 30° C.) and replating them in Falcon 75 cm² flasks which had been precoated with gelatin by incubating the growth surface of the flasks overnight with 2% (w/v) of gelatin (Difco) made up in sterile tissue culture grade water. Just before use, the gelatin was aspirated and the flasks were washed with medium. Unlike normal capillary endothelial cells derived from brains of mice, these cells could be repeatedly passaged.

The endothelial cell cultures were examined to determine if these cells made a novel differentiation regulating activity produced by their normal counterparts. Differentiation of O-2A progenitors into type-2 astrocytes requires the presence of at least two appropriate inducing factors, these being ciliary neurotrophic factor and an unknown factor found in the matrix of endothelial or meningeal cultures (Lillien & Raff, 1990, Neuron, 5:111–119). Our own studies have shown that the factor which co-operates with ciliary neurotrophic factor to induce astrocytic differentiation is secreted by a variety of normal endothelial cells, but not by other cell types. The endothelial cell lines produced from H2ts6 transgenic mice are as potent a source of this differentiation stabilizing activity as are any of the nontransgenic endothelial cells which have thus far been examined.

The assay employed to recognize the endothelial cell-derived factor which works co-operatively with ciliary neurotrophic factor is to prepare cultures of optic nerve cells from nerves of 7 day old rats by standard methods (e.g., Raff et al., 1983, Nature, 303:390–396) and grow these cells at a density of 3000–5000 cells per cover slip in the presence of chemically-defined medium (prepared as in Raff et al., 1983, Nature, 303:390–396) which has been conditioned for 24 hours by confluent cultures of bovine aortic endothelial cells. O-2A progenitor cells grown in this manner all turn into type-2 astrocytes within 4 days of in vitro growth, while cells grown in chemically-defined medium which is not conditioned by endothelial cells all turn into oligodendrocytes. The type-2 astrocytes are recognized as being stellate cells which are GFAP+ and are also labeled with the A2B5 monoclonal antibody.

Examination of medium conditioned by the endothelial cell lines prepared from cerebral cortices of H2ts6 mice demonstrates that these endothelial cells secrete a biological activity indistinguishable from that secreted by nontransgenic endothelial cells in terms of both effect and protency.

EXAMPLE 7

Colonic Epithelial Cells (1) This Example demonstrates that the invention allows the direct immortalization of a novel category of epithelial cells which have proven intractable to the application of in vitro methods of gene insertion for the generation of immortalized cell lines.

Colons were removed from 14–18 day old H2ts6 mice. The colons were sterilized by washing them in 0.04% sodium hypochlorite (in PBS). In some cases, crypts were removed from the colons by incubating tissue for 1.5 h in 3 mM EDTA+0.05 mM dithiothreitol. Tissue was washed with PBS and then shaken by hand which results in the dislodging of intact crypts from the surrounding tissue. These crypts, which are seen as a finger-shaped group of cells are then grown in monolayer culture on a substrate of rat-tail collagen on a medium of Dulbeccco's Modified Eagle's Medium containing the defined chemical additives specified in Raff et al. (1983, Nature, 303:390–396) plus 2% fetal calf serum+20 U/ml of IFN-gamma+20% conditioned medium (conditioned for 24 h) from tumour line LIM 1863 (Whitehead et al., 1987, Cancer Res., 47:2683–2689). Crypts sit down and epithelium starts to spread out. With nontransgenic crypts, cells will remain viable on a feeder layer of bovine aortic endothelial cells, although they cannot be passaged (Whitehead et al., 1991, J. Tissue Cult. Methods (in press)). In contrast, cells derived from the transgenic animals can be grown and passaged without a feeder layer and set up in monolayer culture. In other cases, the colons were grown in explant culture. The medium used throughout was as described above. Cultures were fed two–three times a week, with fresh addition of interferon with each feeding.

The crypt cultures gave rise to patches of flat cells with a clear epithelioid morphology, while explant cultures gave rise to mixed cultures containing a number of morphologically distinct cell types. The epithelioid cells derived from the crypts are labeled with two anti-keratin antibodies (LE 61 and LP 34, as cited in Lane, vide infra), and labeling shows a characteristic fibrillary pattern of cytoplasmic staining.

Use of these mice has thus provided the means for establishing colonic epithelial cells in culture in a manner that was previously impossible and from tissues that have previously been impossible to culture for more than 24–48 hours. The major cell types of interest in the explant cultures are discussed in the following Example.

EXAMPLE 8

Glial Cells of the Enteric Nervous System

Explant cultures of colon, prepared as described in the previous Example, contained two cell types of particular interest. One of these cells was a small processing cell which was labeled with antibodies against GFAP, thus identifying this cell as one of the glial cells of the enteric nervous system. These cells have been readily passaged, and should be readily convertible to cell lines. Although there is considerable interest in the glial cells of the enteric nervous system, no cell lines have been described for this tissue to date.

The second cell type had a fibroblast like morphology and did not label with anti-GFAP antibodies. However, upon treatment with transforming growth factor-beta, these cells are induced to express nestin, an intermediate filament protein thought to be specifically expressed by precursor cells of the central nervous system (Lendahl, Cell, 1990, 60:585–595). The normal cellular counterpart of these cells is not known, but their induced expression of nestin raises the possibility that these cells are a novel precursor population.

EXAMPLE 9

Myoblasts (1) The Example demonstrates that cell lines generated by the method of the invention retain their capacity to undergo normal differentiation in vitro.

(2) This Example further demonstrates that cell lines derived from the H2ts6 mice have the capacity to undergo normal differentiation in vivo, thus indicating the potential usefulness of cell lines derived from the H2ts6 mice in cell transplantation applications.

Clonal myoblast cultures were prepared by direct limiting dilution cloning of cells derived from dissection of skeletal muscle from hindlegs of neonatal mice into standard tissue culture conditions for the growth of muscle precursor cells (as described, e.g., in Morgan et al., 1987, J. Muscle Res. and Cell Motil., 8:386–396), except that cells were grown at 33° C. in the presence of gamma-interferon. Clonal cultures were grown continuously for several weeks, and were passaged repeatedly, before transplantation of cells directly into the skeletal muscle mass of nontransgenic mice bearing a known mutation of the dystrophin gene. The dystrophin gene mutation means that this protein shows abnormal localization within the multinucleated myotubes which are formed by fusion and differentiation of muscle precursor cells. The transplanted cells derived from transgenic mice could be readily identified by the fact that they generated skeletal myotubes which expressed normal dystrophin. In addition, the muscle precursor cells derived from the H2ts6 transgenic mice were able to fuse into multinucleate myotubes in vivo by either growing cells at high density or turning off oncogene expression by growth of cells in non-permissive conditions.

Cell lines of the present invention, in which expression of the differentiation inhibiting gene is regulated, differ from currently available cell lines in that it is theoretically possible to obtain cell lines from any tissue of the body and select for cell lines of any identity. Thus, the present technique differs qualitatively from previous techniques in which genetic information was transfected or infected into cells in a manner which does not allow targeting of particular populations or reliable immortalization of rare cells. With this new technique, rare cells can be isolated by any means available in the art (e.g., fluorescence-activated cell sorting, density centrifugation, panning, immunoselection with magnetic beads, selective adhesion to defined protein or carbohydrate substrates, etc.) and grown in conditions which support activation of the differentiation inhibiting gene, and thus allow the rare cells to be grown in large quantities. Any use to which such cells can be put thus becomes a real practical possibility for the first time, including (but not limited to) the isolation of cellular components or substances from such rare cells.

Immortalized cells or differentiated cells derived from animals of the invention have a number of important uses, including, inter alia, the following specific further aspects of the invention:

A) The use of either immortalized cells which have been obtained by a method as defined above or of differentiated cells derived therefrom or of cells isolated from an animal of the invention and wherein expression of said differentiation inhibiting sequence has been activated but which cell may nonetheless be induced to differentiate by exposure to an external factor and have been so exposed or of cells isolated from an animal of the invention which have been grown in vitro and a non-conditional immortalizing gene or genes thereafter inserted in vitro, either as a source of a cell-produced substance, optionally a growth or differentiation factor, or in an assay system in relation to such a substance (in one illustrative embodiment of this use, the cell-produced substance is an antibody);

B) The use either of immortalized cells which have been obtained by a method as defined above or of differentiated cells derived therefrom or of cells isolated from an animal of the invention and wherein expression of said differentiation inhibiting sequence has been activated but which cell may nonetheless be induced to differentiate by exposure to an external factor and have been so exposed or of cells isolated from an animal of the invention which have been grown in vitro and a non-conditional immortalizing gene or genes thereafter inserted in vitro, in the production of a medicament, either: said medicament being for the treatment or prophylaxis of a condition characteristic of a cell deficiency or cell-produced factor deficiency or of a cellular malfunction by cell transplantation; or said medicament comprising a cell-produced factor derived from any of the aforesaid cells;

C) An extremely important aspect is a method of therapy or prophylaxis practised on the human or animal body which comprises administering either: immortalized cells which have been obtained by a method as defined above or differentiated cells derived therefrom or cells isolated from an animal of the invention wherein expression of said differentiation inhibiting sequence has been activated but which cells may nonetheless be induced to differentiate by exposure to an external factor and have been so exposed or cells isolated from an animal of the invention which have been grown in vitro and a non-conditional immortalizing gene or genes thereafter inserted in vitro; or a factor derived from any of the aforesaid cells. Particular embodiments are methods of transplantation therapy practised on the human or animal body and in which immortalized cells which have been obtained by a method as defined above or differentiated cells derived therefrom by deactivating expression of said differentiation inhibiting sequence or cells isolated from an animal of the invention and wherein expression of said differentiation inhibiting sequence has been activated but which cells may nonetheless be induced to differentiate by exposure to an external factor and have been so exposed or cells isolated from an animal of the invention which have been grown in vitro and a non-conditional immortalizing gene or genes thereafter inserted in vitro, are transplanted into said body under conditions either allowing differentiation of immortalized cells to occur or preventing expression of the differentiation inhibiting sequence in the case of differentiated cells, with consequent compensation for a deficiency of or malfunction in pre-existing cells in said body (in two illustrative embodiments of such methods, the transplanted cells are either insulin-producing cells from the pancreas of said animal or precursor cells therefor, the transplantation therapy being for the treatment or prophylaxis of an insulin-deficiency disease, or glial cells or glial precursor cells, the transplantation therapy being for the treatment or prophylaxis of a disease or disorder of the nervous system); and D) The use of immortalized cells which have been obtained by a method as defined above or of differentiated cells derived therefrom or of cells isolated from an animal of the invention and wherein expression of said differentiation inhibiting sequence has been activated but which cells may nonetheless be induced to differentiate by exposure to an external factor and have been so exposed or of cells isolated from an animal of the invention which have been grown in vitro and a non-conditional immortalizing gene or genes thereafter inserted in vitro, in a method of in vitro diagnosis.

Cell lines are already routinely used as assay systems in the purification of factors which stimulate cell division and differentiation. Cell lines can also be used as assay systems for the purification of genes which regulate division and differentiation. Many of the established oncogenes were identified by virtue of their ability to convert established cell lines to a neoplastic state. Genes which induce cells to differentiate into specific cell types can also be identified by transfection of genetic material into suitable recipient cells, as evidenced by recent studies on the identification of genes which control muscle cell differentiation. One could envisage, e.g., using insulin-negative pancreatic cell lines as suitable assay systems for the identification of factors or genes which induce some pancreatic cells to produce insulin.

In general, the present invention provides a means by which large numbers of differentiated cells or precursor cells can be produced. For example, if a large quantity of a specific type of cell is needed for use in diagnostic methods, for transplantation into an individual or for use as a means of producing a desired product (e.g., a mitogen or differentiation factor), then appropriate cells can be selected using known techniques. These cells can subsequently be grown in permissive conditions for a desired amount of time. The cells can be studied in permissive conditions, wherein induction of at least some aspects of differentiation appears to be possible. In addition, cells can be switched to non-permissive conditions compatible with more extensive differentiation along normal pathways. Moreover, cells can be genetically manipulated in tissue culture so as to express a wild-type differentiation-inhibiting sequence, thus allowing the growth of large numbers of cells (e.g., for purposes of purification of a desired protein produced by the cells) without the continued use of permissive growth conditions.

It is clear from the principles of the present invention that conditionally immortalized cells obtained from the present transgenic animals can be introduced (in non-permissive conditions) into an individual, in whom they will reside in a non-permissive environment. The introduction of such cells is invaluable for the development of precursor transplantation therapies in which large numbers of precursor cells are transplanted into diseased tissue in order to replenish the populations required for normal function. For example, insulin producing cells derived from the pancreas of a transgenic animal of this invention can be surgically implanted into the pancreas of animals suffering from insulin-deficiency diseases (such as type I diabetes).

The use of genetically engineered cells to enhance regenerative processes or restore tissue function has become of increasing practical interest. For example, Gage and colleagues (Science, 1988, 242, 1575) described the injection of fibroblasts genetically engineered to overproduce nerve growth factor into the site of a fimbria-fornix lesion. These transplanted cells prevented retrograde axonal degeneration for at least 2 weeks in initial studies, and more recently have been shown to promote survival of the cholinergic neurons for up to 8 weeks (Rosenberg, et al, 1985 Am. Soc. Neurosci. Abs. No. 433.2).

Many tumours are histologically related to cells found in the early stages of tissue development. The animals of the present invention provide a ready source of cells for the identification of potential precursors of tumour cells. In addition to the strategy already discussed in relation to the identification of a putative glioma precursor cell, it will also be possible to use other technologies of gene insertion (e.g., transfection, electroporation, retroviral-mediated gene insertion) to further manipulate the genome of any of the cell lines isolated from the animals of the present invention.

Thus, specific precursors or differentiated cell types can be initially grown in numbers large enough to allow utilization of less efficient methods of gene insertion and these further modified cells can be utilized in the study of neoplastic transformation of defined cell types.

Furthermore, the animals of the present invention provide a means of obtaining immortalized cell lines exhibiting preselected mutations. A further aspect of the invention is thus use of an animal of the invention as a parent for crossing with a mutant animal parent which expresses a preselected mutation in producing a descendant mutant animal exhibiting normal cell development and from which immortalizable cells expressing said mutation may be isolated. Preferably, in such a use both parents are homozygous for those of their respective traits which must be exhibited by an descendant as defined above. The invention accordingly includes a further aspect which is cells, immortalized or immortalizable, expressing said preselected mutation and derived from a descendant as defined and produced above.

It will be apparent to the skilled reader that various modifications and alterations may be made to the various embodiments discussed and/or described above without departing from the scope of the present inventive concept.

We claim:

1. Method for establishing a cell in culture comprising:
   (i) removing a cell from a transgenic mouse, wherein said cell has chromosomally integrated a DNA sequence encoding TAgts protein under the control of a non-constitutive promotor wherein expression of said TAgts protein has been at a sufficiently low functional level in vivo to permit normal development of said cell in said mouse, and
   (ii) subjecting the removed cell to permissive conditions in culture, wherein said permissive conditions lead to a functional level of expression of said TAgts protein sufficient to prevent complete differentiation of said cell.

2. Method of claim 1, wherein expression of said TAgts protein in culture immortalizes said cell.

3. Method of claim 1, wherein said promotor comprises a plurality of genetic regulatory elements in operable association.

4. Method of claim 1, wherein said promotor is a major histocompatability complex, class I antigen promotor.

5. Isolated cell obtained by the method of claim 1 after step (ii).

6. Cell line produced by culturing a cell isolated by the method of claim 1 after step (ii) under conditions favoring division thereof.

7. Method of claim 1, wherein said cell is a precursor cell.

8. Method of claim 1, wherein said cell is selected from the group consisting of a pancreatic cell, a precursor of an insulin producing cell, a glial cell, a glial cell precursor, a muscle cell, and a muscle cell precursor.

9. Method for producing an expression product of the cell of claim 5, comprising culturing said cell under conditions factoring production of said expression product.

10. Method for producing an expression product of the cell line of claim 6 comprising culturing said cell line under conditions favoring production of said expression product.

11. Method for establishing a cell in culture comprising:

(i) removing a cell from a transgenic mouse, wherein said cell has chromosomally integrated a DNA sequence encoding TAgts protein under the control of a H-2K$^b$ promotor wherein expression of said TAgts protein is at a sufficiently low functional level in vivo to permit normal development of said cell in said mouse, and (ii) subjecting the removed cell to permissive conditions in culture, wherein said permissive conditions lead to a functional level of expression of said TAgts protein sufficient to prevent complete differentiation of said cell.

12. Method of claim 11, wherein expression of said TAgts protein in culture immortalizes said cell.

13. Isolated cell obtained by the method of claim 11 after step (ii).

14. Cell line produced by culturing a cell isolated by the method of claim 11 after step (ii) under conditions favoring division thereof.

15. Method of claim 11, wherein said cell is a precursor cell.

16. Method of claim 11, wherein said cell is selected from the group consisting of a pancreatic cell, a precursor of an insulin producing cell, a glial cell, a glial cell precursor, a muscle cell, and a muscle cell precursor.

17. Method for producing an expression product of the cell of claim 13 comprising culturing said cell under conditions favoring production of said expression product.

18. Method for producing an expression product of the cell line of claim 14 comprising culturing said cell line under conditions favoring production of said expression product.

* * * * *

UNITED STATES PATENT AND TRADEMARK OFFICE
CERTIFICATE OF CORRECTION

PATENT NO. : 5,688,692
DATED     : Jat, et. al.
INVENTOR(S) : November 18, 1997

It is certified that error appears in the above-identified patent and that said Letters Patent is hereby corrected as shown below:

Title apge, item [30] Foreign Application Priority Data, change "9003791" to -- 9003791.2--.

In column 14, lines 38-39, change "(Jat and Sharp, 1989 Mol." to - - Jat and Sharp, 1989 Mol: Cell Biol. 9, 1672 - 1681). - -.

Signed and Sealed this

Twenty-seventh Day of June, 2000

Attest:

Q. TODD DICKINSON

*Attesting Officer*  *Director of Patents and Trademarks*